(12) United States Patent
Scheidt et al.

(10) Patent No.: US 11,485,734 B2
(45) Date of Patent: Nov. 1, 2022

(54) BETA-CARBOLINES AS POSITIVE ALLOSTERIC MODULATORS OF THE HUMAN SEROTONIN RECEPTOR 2C (5-HT$_{2C}$)

(71) Applicant: Northwestern University, Evanston, IL (US)

(72) Inventors: Karl A. Scheidt, Evanston, IL (US); Herbert Y. Meltzer, Chicago, IL (US); Adam J. Csakai, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/766,217

(22) PCT Filed: Oct. 2, 2019

(86) PCT No.: PCT/US2019/054337
§ 371 (c)(1),
(2) Date: May 21, 2020

(87) PCT Pub. No.: WO2020/072675
PCT Pub. Date: Apr. 9, 2020

(65) Prior Publication Data
US 2021/0214352 A1 Jul. 15, 2021

Related U.S. Application Data

(60) Provisional application No. 62/740,084, filed on Oct. 2, 2018.

(51) Int. Cl.
| | | |
|---|---|---|
| *C07D 471/04* | (2006.01) | |
| *A61P 25/36* | (2006.01) | |
| *A61P 25/28* | (2006.01) | |
| *A61P 3/04* | (2006.01) | |
| *A61P 25/18* | (2006.01) | |

(52) U.S. Cl.
CPC .............. *C07D 471/04* (2013.01); *A61P 3/04* (2018.01); *A61P 25/18* (2018.01); *A61P 25/28* (2018.01); *A61P 25/36* (2018.01)

(58) Field of Classification Search
CPC .......... A61P 25/46; A61P 25/38; A61P 25/28; A61P 3/04
See application file for complete search history.

(56) References Cited

U.S. PATENT DOCUMENTS

| | | |
|---|---|---|
| 3,915,990 A | 10/1975 | Smythies |
| 4,435,403 A | 3/1984 | Braestrup |
| 4,631,149 A * | 12/1986 | Rinehart, Jr. ......... C07D 515/14 540/546 |
| 6,350,757 B1 | 2/2002 | Goldstein |
| 6,433,175 B1 | 8/2002 | Adams |
| 6,890,933 B1 | 5/2005 | Feng |
| 7,348,336 B2 | 3/2008 | Ritzeler |
| 7,732,447 B2 | 6/2010 | Becknell |
| 7,855,295 B2 | 12/2010 | Wang |
| 7,872,133 B2 | 1/2011 | Ohmoto |
| 8,071,786 B2 | 12/2011 | Sard |
| 8,076,352 B2 | 12/2011 | Cao |
| 8,329,723 B2 | 12/2012 | Buolamwini |
| 8,742,141 B2 | 6/2014 | Bergan |
| 8,754,132 B2 | 6/2014 | Kozikowski |
| 8,912,341 B2 | 12/2014 | Scheidt |
| 8,927,570 B2 | 1/2015 | Buolamwini |
| 9,260,564 B2 | 2/2016 | Lombardo |
| 9,309,217 B2 | 4/2016 | Scheidt |
| 9,334,297 B2 | 5/2016 | Scheidt |
| 9,365,521 B2 | 6/2016 | Blackbum |
| 9,440,976 B2 | 9/2016 | Dyke |
| 9,512,146 B2 | 12/2016 | Scheidt |
| 9,527,812 B2 | 12/2016 | Scheidt |

(Continued)

FOREIGN PATENT DOCUMENTS

| | | |
|---|---|---|
| AU | 762958 B2 | 7/2000 |
| CN | 104003988 A | 8/2014 |

(Continued)

OTHER PUBLICATIONS

Wiertek et al., 23(4) Archivum Immunologiae et Therapiae Experimentalis 581-7 (1975) (Year: 1975).*
LeBoeuf et al., (5) J. Chem. Soc., Perkins Trans. 1: Org. & Bio-Org. Chem. (1972-1999) 1205-8 (1982) (Year: 1982).*
Abramyants, M. G., et al. "Dehydrogenation of 1-aryl (hetaryl)-1, 2, 3,4-tetrahydro-9H-β-carboline-3-carboxylic acids and their esters with dimethyl sulfoxide." Russian Journal of Organic Chemistry 52.11 (2016): 1610-1615.
Abranyi-Balogh, P., et al. "Synthetic study on the T3P®-promoted one-pot preparation of 1-substituted-3, 4-dihydro-β-carbolines by the reaction of tryptamine with carboxylic acids." Tetrahedron Letters 57.18 (2016): 1953-1957.
Boursereau, Y., et al. "Synthesis and biological studies of 1-amino β-carbolines." Bioorganic & medicinal chemistry letters 14.23 (2004): 5841-5844.

(Continued)

*Primary Examiner* — Timothy R Rozof
(74) *Attorney, Agent, or Firm* — Quarles & Brady LLP

(57) ABSTRACT

Disclosed are novel small molecules, methods of synthesis of the small molecules, and uses of the small molecules for modulating activity of the human serotonin receptor 2C (5-HT$_{2C}$), preferably selectively. The small molecules have a substituted beta-carboline core structure, which optionally may be saturated at one or more bonds to provide a dihydro-beta-carboline core or a tetrahydro-beta-carboline core. The small molecules may be administered to treat and/or prevent diseases, disorders, and/or conditions associated with human serotonin receptor 2C (5-HT$_{2C}$) including psychiatric, mental, and/or neurological diseases, disorders, and conditions such as cognitive impairment, addiction, and obsessive compulsive disorder. The disclosed small molecules also may be administered to treat and/or prevent obesity, for example, via appetite suppression.

16 Claims, 8 Drawing Sheets

(56) References Cited

U.S. PATENT DOCUMENTS

| | | |
|---|---|---|
| 9,533,973 B2 | 1/2017 | Zhou |
| 9,624,190 B2 | 4/2017 | Scheidt |
| 9,643,947 B2 | 5/2017 | Scheidt |
| 9,839,625 B2 | 12/2017 | Bergan |
| 9,840,487 B2 | 12/2017 | Scheidt |
| 9,981,968 B2 | 5/2018 | Schiltz |
| 10,011,614 B2 | 7/2018 | Wang |
| 10,226,471 B2 | 3/2019 | Shao |
| 10,231,949 B2 | 3/2019 | Bergan |
| 10,308,624 B2 | 6/2019 | Scheidt |
| 10,323,039 B2 | 6/2019 | Scheidt |
| 10,654,865 B2 | 5/2020 | Scheidt |
| 10,780,076 B2 | 9/2020 | Bergan |
| 10,781,172 B2 | 9/2020 | Scheidt |
| 11,174,238 B2 | 11/2021 | Scheidt |
| 11,225,483 B2 | 1/2022 | Schiltz |
| 2005/0282849 A1 | 12/2005 | Moon |
| 2006/0264418 A1 | 11/2006 | Galka |
| 2007/0254878 A1 | 11/2007 | Cao |
| 2009/0143363 A1 | 6/2009 | Liu |
| 2009/0203750 A1 | 8/2009 | Kozikowski |
| 2009/0318527 A1 | 12/2009 | Sard |
| 2010/0125065 A1 | 5/2010 | Young-Choon |
| 2011/0178053 A1 | 7/2011 | Arendt |
| 2011/0218193 A1 | 9/2011 | Kim |
| 2013/0296582 A1 | 11/2013 | Bergan |
| 2015/0065703 A1 | 3/2015 | Scheidt |
| 2015/0247004 A1 | 9/2015 | Lombardo |
| 2015/0315143 A1 | 11/2015 | Scheidt |
| 2015/0315168 A1 | 11/2015 | Scheidt |
| 2016/0002252 A1 | 1/2016 | Schiltz |
| 2016/0024120 A1 | 1/2016 | Scheidt |
| 2016/0039845 A1 | 2/2016 | Wang |
| 2016/0075728 A1 | 3/2016 | Scheidt |
| 2016/0128973 A1 | 5/2016 | Bergan |
| 2016/0326183 A1 | 11/2016 | Scheidt |
| 2017/0212992 A1 | 7/2017 | Pah |
| 2017/0283413 A1 | 10/2017 | Zhang |
| 2018/0153853 A1 | 6/2018 | Bergan |
| 2018/0170941 A1 | 6/2018 | Mekonnen |
| 2018/0265453 A1 | 9/2018 | Kozikowski |
| 2019/0031672 A1 | 1/2019 | Cunningham |
| 2019/0201373 A1 | 7/2019 | Bergan |
| 2019/0276458 A1 | 9/2019 | Schiltz |
| 2019/0300540 A1 | 10/2019 | Scheidt |
| 2019/0389798 A1 | 12/2019 | Scheidt |
| 2020/0181106 A1 | 6/2020 | Scheidt |
| 2020/0399241 A1 | 12/2020 | Scheidt |
| 2021/0002221 A1 | 1/2021 | Scheidt |
| 2021/0009547 A1 | 1/2021 | Scheidt |
| 2021/0009603 A1 | 1/2021 | Scheidt |
| 2021/0024473 A1 | 1/2021 | Scheidt |
| 2021/0070725 A1 | 3/2021 | Scheidt |

FOREIGN PATENT DOCUMENTS

| | | |
|---|---|---|
| CN | 106957301 A | 7/2017 |
| CN | 108409732 A | 8/2018 |
| DE | 2315989 A1 | 10/1973 |
| DE | 3240514 A1 | 10/1982 |
| EP | 0161574 B1 | 3/1987 |
| EP | 2455378 A1 | 5/2012 |
| EP | 3318563 A1 | 5/2018 |
| FR | 2953837 A1 | 6/2011 |
| FR | 2953838 A1 | 6/2011 |
| NZ | 505903 A | 8/2001 |
| WO | 1988000826 A1 | 2/1988 |
| WO | 2001068648 A1 | 9/2001 |
| WO | 2003037898 A1 | 5/2003 |
| WO | 2003082866 A1 | 10/2003 |
| WO | 2003086306 A2 | 10/2003 |
| WO | 2005089764 A1 | 9/2005 |
| WO | 2005070930 A2 | 1/2006 |
| WO | 2006116151 A1 | 11/2006 |
| WO | 2007101863 A1 | 9/2007 |
| WO | 2007149557 A1 | 12/2007 |
| WO | 2008117169 A1 | 10/2008 |
| WO | 2009151598 A1 | 12/2009 |
| WO | 2010123583 A2 | 10/2010 |
| WO | 2010138758 A1 | 12/2010 |
| WO | 2011070298 A1 | 6/2011 |
| WO | 2011070299 A1 | 6/2011 |
| WO | 2011073263 A1 | 6/2011 |
| WO | 2012059232 A1 | 5/2012 |
| WO | 2014063477 A1 | 5/2014 |
| WO | 2015197861 A1 | 12/2015 |
| WO | 2017087534 A1 | 5/2017 |
| WO | 2018035477 A1 | 2/2018 |
| WO | 2018083157 A1 | 5/2018 |
| WO | 2018206537 A1 | 11/2018 |
| WO | 2018214222 A1 | 11/2018 |

OTHER PUBLICATIONS

Costa, E. V., et al. "Full NMR analysis of annomontine, methoxy-annomontine and N-hydroxyannomontine pyrimidine-β-carboline alkaloids." Magnetic Resonance in Chemistry 46.1 (2008): 69-74.

Durham, S. D., et al. "Synthesis of β-carbolines via a silver-mediated oxidation of tetrahydro-β-carbolines." Tetrahedron Letters 58.28 (2017): 2747-2750.

Eagon, S., et al. "Microwave-Assisted Synthesis of Tetrahydro-β-carbolines and β-Carbolines." European Journal of Organic Chemistry Aug. 2014 (2014): 1653-1665.

Foley, C. A., et al. "Synthesis and Structure-Activity Relationships of 1-Aryl-β-carbolines as Affinity Probes for the 5-Hydroxytryptamine Receptor." ACS Omega 4.6 (2019): 9807-9812.

Guo, L., et al. "Synthesis and biological evaluation of novel N 9-heterobivalent β-carbolines as angiogenesis inhibitors." Journal of enzyme inhibition and medicinal chemistry 34.1 (2019): 375-387.

Guo, L., et al. "Synthesis and structure-activity relationships of asymmetric dimeric β-carboline derivatives as potential antitumor agents." European journal of medicinal chemistry 147 (2018): 253-265.

Horton, W., et al. "Synthesis and application of β-carbolines as novel multi-functional anti-Alzheimer's disease agents." Bioorganic & medicinal chemistry letters 27.2 (2017): 232-236.

Huang, Y.-Q., et al. "Dehydrogenation of N-Heterocycles by Superoxide Ion Generated through Single-Electron Transfer." Chemistry—A European Journal 24.9 (2018): 2065-2069.

International Searching Authority. International Search Report and Written Opinion for application PCT/US2019/054337, dated Jan. 16, 2020.

Kamal, A., et al. "An efficient one-pot decarboxylative aromatization of tetrahydro-β-carbolines by using N-chlorosuccinimide: total synthesis of norharmane, harmane and eudistomins." RSC advances 5.109 (2015): 90121-90126.

Kamal, A., et al. "PhI (OAc) 2-mediated one-pot oxidative decarboxylation and aromatization of tetrahydro-β-carbolines: synthesis of norharmane, harmane, eudistomin U and eudistomin I." Organic & biomolecular chemistry 13.32 (2015): 8652-8662.

Manasa, K. L., et al. "TCCA; A Mild Reagent for Decarboxylative/Dehydrogenative Aromatization of Tetrahydro-β-carbolines: Utility in the Total Synthesis of Norharmane, Harmane, Eudistomin U, I and N." ChemistrySelect 2.28 (2017): 9162-9167.

Pakhare, D. S., et al. "Synthesis of tetrahydro-β-carbolines, β-carbolines, and natural products,(±)-harmicine, eudistomin U and canthine by reductive Pictet Spengler cyclization." Tetrahedron Letters 56.44 (2015): 6012-6015.

Penjarla, T. R., et al. "Synthesis of 4-Substituted Pyrrolo [2, 3-c] quinolines via Microwave Assisted C—N Bond Formation." ChemistrySelect 3.19 (2018): 5386-5389.

Ramu, S., et al. "Metal free one pot synthesis of β-carbolines via a domino Pictet-Spengler reaction and aromatization." Molecular Catalysis 468 (2019): 86-93.

Reddy, GM, et al. "Highly Site-Selective and Direct Ortho-C—H Nitration, Trifluoromethylation and Cyanation at the C1-Position of Carbazole Frameworks." Asian Journal of Organic Chemistry 6.1 (2017): 59-62.

(56) References Cited

OTHER PUBLICATIONS

Roggero, C. M., et al. "Efficient synthesis of eudistomin U and evaluation of its cytotoxicity." Bioorganic & medicinal chemistry letters 24.15 (2014): 3549-3551.

Ryabukhin, S. V., et al. "Application of chlorotrimethylsilane in Pictet-Spengler reaction." Monatshefte für Chemie-Chemical Monthly 143.11 (2012): 1507-1517.

Saha, B., et al. "Water as an efficient medium for the synthesis of tetrahydro-β-carbolines via Pictet-Spengler reactions." Tetrahedron letters 48.8 (2007): 1379-1383.

Shi, B., et al. "Design, synthesis and in vitro and in vivo antitumor activities of novel bivalent β-carbolines." European Journal of Medicinal Chemistry 60 (2013): 10-22.

Wang, Z.-X., et al. "Direct Biomimetic Synthesis of β-Carboline Alkaloids from Two Amino Acids." The Journal of Organic Chemistry 83.19 (2018): 12247-12254.

Wold, E. A., et al. "Targeting the 5-HT2C receptor in biological context and the current state of 5-HT2C receptor ligand development." Current topics in medicinal chemistry 19.16 (2019): 1381-1398.

Zhang, G., et al. "Discovery of N-substituted (2-phenylcyclopropyl) methylamines as functionally selective serotonin 2C receptor agonists for potential use as antipsychotic medications." Journal of Medicinal Chemistry 60.14 (2017): 6273-6288.

Zhao, Z., et al. "Organic base-promoted efficient dehydrogenative/decarboxylative aromatization of tetrahydro-β-carbolines into β-carbolines under air." Tetrahedron Letters 60.11 (2019): 800-804.

* cited by examiner

BETA-CARBOLINES AS POSITIVE ALLOSTERIC MODULATORS OF THE HUMAN SEROTONIN RECEPTOR 2C (5-HT$_{2C}$)

CROSS-REFERENCED TO RELATED PATENT APPLICATIONS

The present application is the U.S. National Stage Entry of International Application PCT/US2019/054337, filed Oct. 2, 2019, which claims the benefit of priority under 35 U.S.C. § 119(e) to U.S. Provisional Patent Application No. 62/740,084, filed Oct. 2, 2018, the contents of which are incorporated herein by reference in their entireties.

BACKGROUND

The field of the invention relates to novel small molecules, methods of synthesis of the small molecules, and uses of the small molecules for modulating activity of the human serotonin receptor 2C (5-HT$_{2C}$). The small molecules have a substituted beta-carboline core structure, which optionally may be saturated at one or more bonds to provide a dihydro-beta-carboline core or a tetrahydro-beta-carboline core. The small molecules may be administered to treat and/or prevent diseases, disorder, and condition associated with human serotonin receptor 2C (5-HT$_{2C}$) activity including psychiatric, mental, and/or neurological diseases, disorders, and conditions such as cognitive impairment, addiction, and obsessive compulsive disorder Serotonin receptors, otherwise referred to as 5-hydroxytryptamine receptors or 5-HT receptors, are a group of G protein-coupled receptor and ligand-gated ion channels found in the central and peripheral nervous systems. (See Hoyer et al., (1994). "International Union of Pharmacology classification of receptors for 5-hydroxytryptamine (Serotonin)". Pharmacol. Rev. 46 (2): 157-203. PMID 7938165; Frazer et al., "Chapter 13: Serotonin Receptors". In Siegel et al. Basic Neurochemistry: Molecular, Cellular, and Medical Aspects. Philadelphia: Lippincott-Raven. pp. 263-292; and Beliveau et al. (2017-01-04). "A High-Resolution In Vivo Atlas of the Human Brain's Serotonin System". Journal of Neuroscience. 37 (1): 120-128. doi:10.1523/jneurosci.2830-16.2016; the contents of which are incorporated herein by reference in their entireties). Serotonin receptors mediate excitatory neurotransmission and inhibitory neurotransmission. The serotonin receptors, as they name indicates, are activated by the neurotransmitter serotonin, which is their natural ligand. Serotonin receptors modulate the release of many neurotransmitters, including glutamate, GABA, dopamine, epinephrine/norepinephrine, and acetylcholine, as well as many hormones, including oxytocin, prolactin, vasopressin, cortisol, corticotropin, and substance P, among others. The serotonin receptors influence various biological and neurological processes such as aggression, anxiety, cognition, learning, memory, mood, appetite, nausea, sleep, and thermoregulation. (See Nichols et al., (May 2008). "Serotonin receptors." Chem. Rev. 108(5): 1614-41; the content of which is incorporate herein by reference in its entirety).

The 5-HT$_2$ family of serotonin receptors mediates excitatory neurotransmission via a G$_q$/G$_{11}$-protein coupled molecular mechanism that increases cellular levels of inositol triphosphate (IP$_3$) and diacylglycerol (DAG). The 5-HT-2 family includes three members: 5-HT$_{2a}$, 5-HT$_{2b}$, and 5-HT$_{2c}$. The 5-HT$_{2a}$ receptor modulates addiction, anxiety, appetite, cognition, imagination, learning, memory, mood, perception, sexual behavior, sleep, thermoregulation, and vasoconstriction. The 5-HT$_{2b}$ receptor modulates anxiety, appetite, cardiovascular function, gastrointestinal motility, sleep, and vasoconstriction. The 5-HT$_{2c}$ receptor modulates addiction, anxiety, appetite, gastrointestinal motility, locomotion, mood, penile erection, sexual behavior, sleep, thermoregulation, and vasoconstriction. Notably, the 5-HT$_{2a}$, 5-HT$_{2b}$, and 5-HT$_{2c}$ exhibit differing affinities for agonists and antagonists and may function as heteroreceptors for ligands other than serotonin. For example, 5-HT$_{2c}$ receptor is a heteroreceptor for norepinephrine and dopamine.

Here, we disclose novel substituted beta-carboline compounds which function as positive allosteric modulators of the human serotonin receptor 2C (5-HT$_{2c}$). The disclosed small molecules preferably act selectively as positive allosteric modulators of the human serotonin receptor 2C (5-HT$_{2c}$), relative to other 5-HT receptors such as 5-HT$_{2a}$, 5-HT$_{2b}$. As such, the small molecules may be administered to treat and/or prevent diseases, disorder, and condition associated with human serotonin receptor 2C (5-HT$_{2c}$) including psychiatric, mental, and/or neurological diseases, disorders, and conditions such as cognitive impairment, addiction, and obsessive compulsive disorder.

SUMMARY

Disclosed are novel small molecules, methods of synthesis of the small molecules, and uses of the small molecules for modulating activity of the human serotonin receptor 2C (5-HT$_{2c}$), preferably selectively. The small molecules have a substituted beta-carboline core structure, which optionally may be saturated at one or more bonds to provide a dihydro-beta-carboline core or a tetrahydro-beta-carboline core. The small molecules may be administered to treat and/or prevent diseases, disorders, and/or conditions associated with human serotonin receptor 2C (5-HT$_{2c}$) including psychiatric, mental, and/or neurological diseases, disorders, and conditions such as cognitive impairment, addiction, and obsessive compulsive disorder (OCD). The disclosed small molecules also may be administered to treat and/or prevent obesity, for example, via appetite suppression.

Significant differences were observed in the DI; *** p<0.001—significant decrease in DI in Vehicle versus PCP group. ###p<0.001—significant increase in DI in PCP versus PCP+AJC-61, one-way ANOVA followed by post-hoc Bonferroni.

Figure 4:
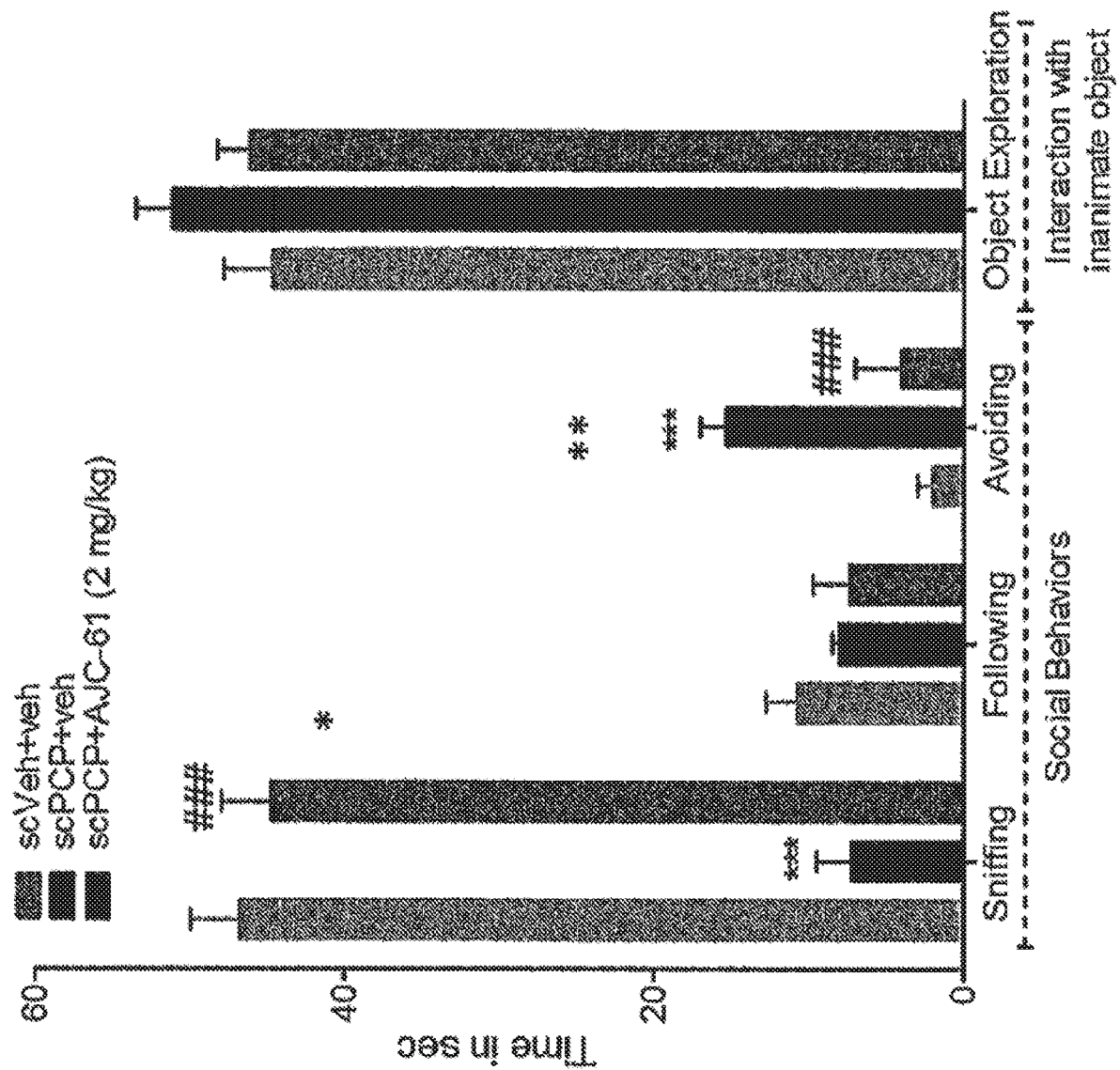

FIG. 4. Social Interaction: Effect of Vehicle, PCP (10 mg/kg: i.p., 7 days: b.i.d.), and PCP+AJC-61 (2 mg/kg), on social behaviors (sniffling, following, and avoiding) and interaction with inanimate object (object exploration), in a 10-minute social interaction (SI) paradigm. Data were analyzed by one-way ANOVA comparing the effect of drug treatment on each behavior and are shown as mean±S.E.M. of time (s); n=10 pairs of mice per group. Sniffing—*p, 0.001: Significant reduction for PCP versus Vehicle group; ###p<0.001; Significant increase for PCP+AJC-61 versus PCP group. Following—No significant change, although there was non-significant reduction in following in the PCP versus Vehicle group. Avoiding—* p<0.001: Significant increase for PCP versus Vehicle group; ###p<0.001: Significant decrease for PCP+AJC-61 versus PCP group. Object Exploration—No significant change, although there was a non-significant increase in object exploration in the PCP versus Vehicle group.

Figure 5:
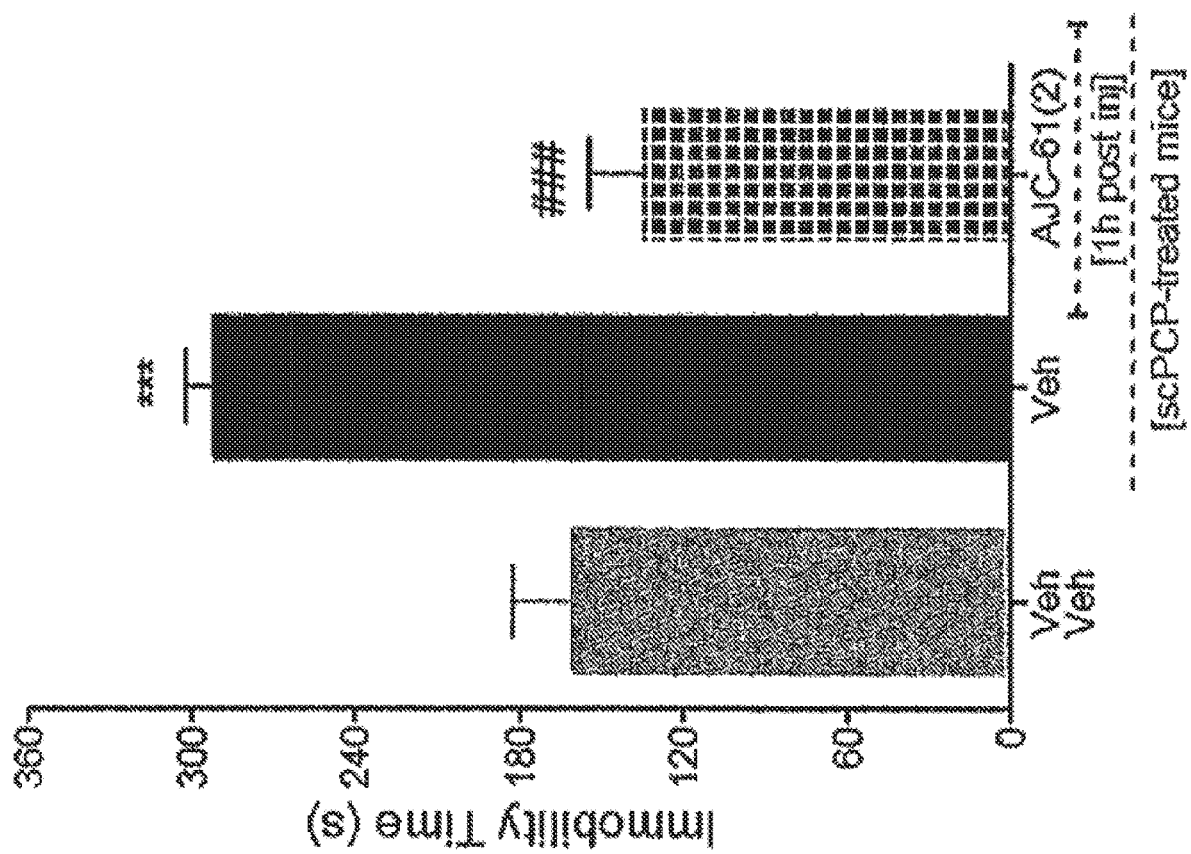

FIG. 5. Porsolt Forced Swim Test (FST). Effect of Vehicle, PCP (10 mg/kg; i.p., 7 days; b.i.d.), and PCP+AJC-61 (2 mg/kg), in a 6-min Porsolt Forced Swim Test (FST). Data were analyzed by one-way ANOVA comparing the effect of drug treatment on each behavior and are shown as mean±S.E.M. of time (s): n=12 pairs of mice per group. *** p<0.001: Significant increase in immobility time for PCP versus Vehicle group; ###p<0.001: Significant decrease in immobility time for PCP+AJC-16 versus PCP group.

Figure 6:
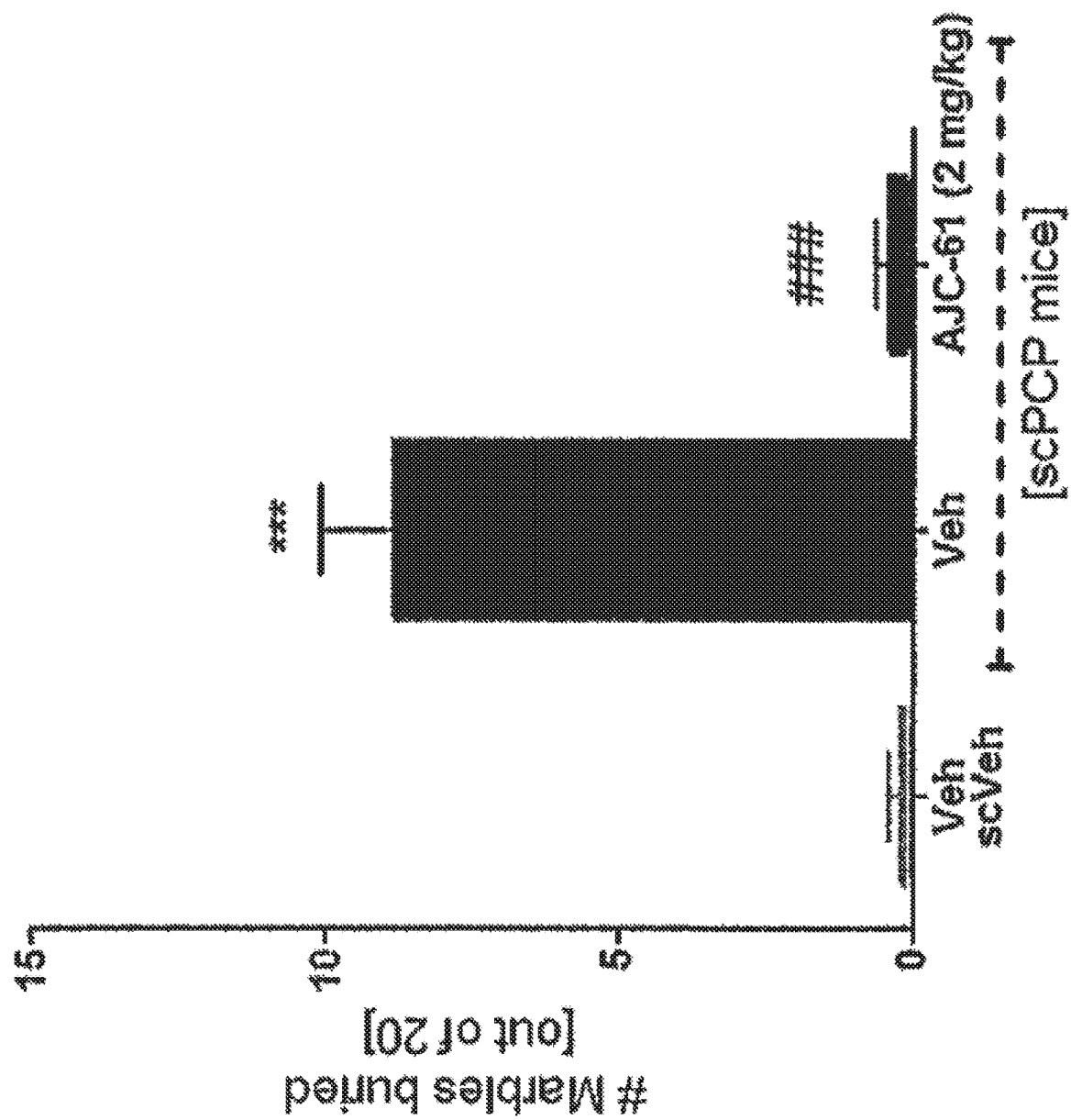

FIG. 6. Marble Burying Task (MBT): Effect of Vehicle, PCP (10 mg/kg; i.p., 7 days; b.i.d.), and PCP+AJC-61 (2 mg/kg) in a 30-minute Marble Burying Task (MBT) paradigm. Data were analyzed by one-way ANOVA comparing the effect of drug treatment on each behavior and are shown as mean±S.E.M. of time (s): n=12 pairs of mice per group. *** p<0.001: Significant increase in the number of marbles buried for PCP versus Vehicle group; ###p<0.001: Significant decrease in the number of marbles buried for PCP+AJC-16 versus PCP group.

Figure 7:
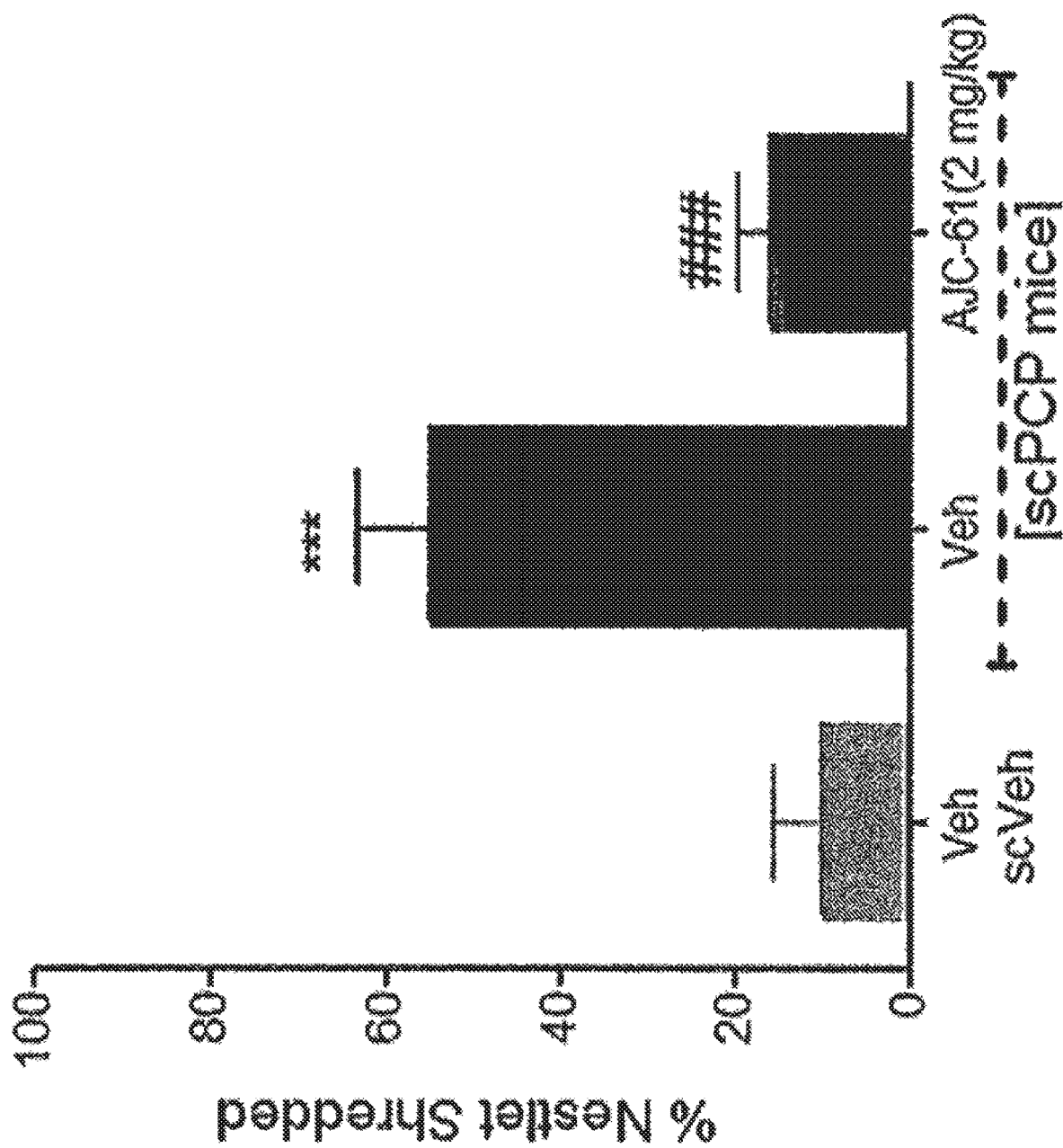

FIG. 7. Nestlet Shredding (NS): Effect of Vehicle, PCP (10 mg/kg; i.p., 7 days; b.i.d.), and PCP+AJC-61 (2 mg/kg) in a 30-minute Nestlet Shredding (NS) paradigm. Data were analyzed by one-way ANOVA comparing the effect of drug treatment on each behavior and are shown as mean±S.E.M. of time (s): n=10 pairs of mice per group. *** p<0.001: Significant increase in the percent nestlet shredded for PCP versus Vehicle group; ###p<0.001: Significant decrease in the percent nestlet shredded for PCP+AJC-16 versus PCP group.

Figure 8:
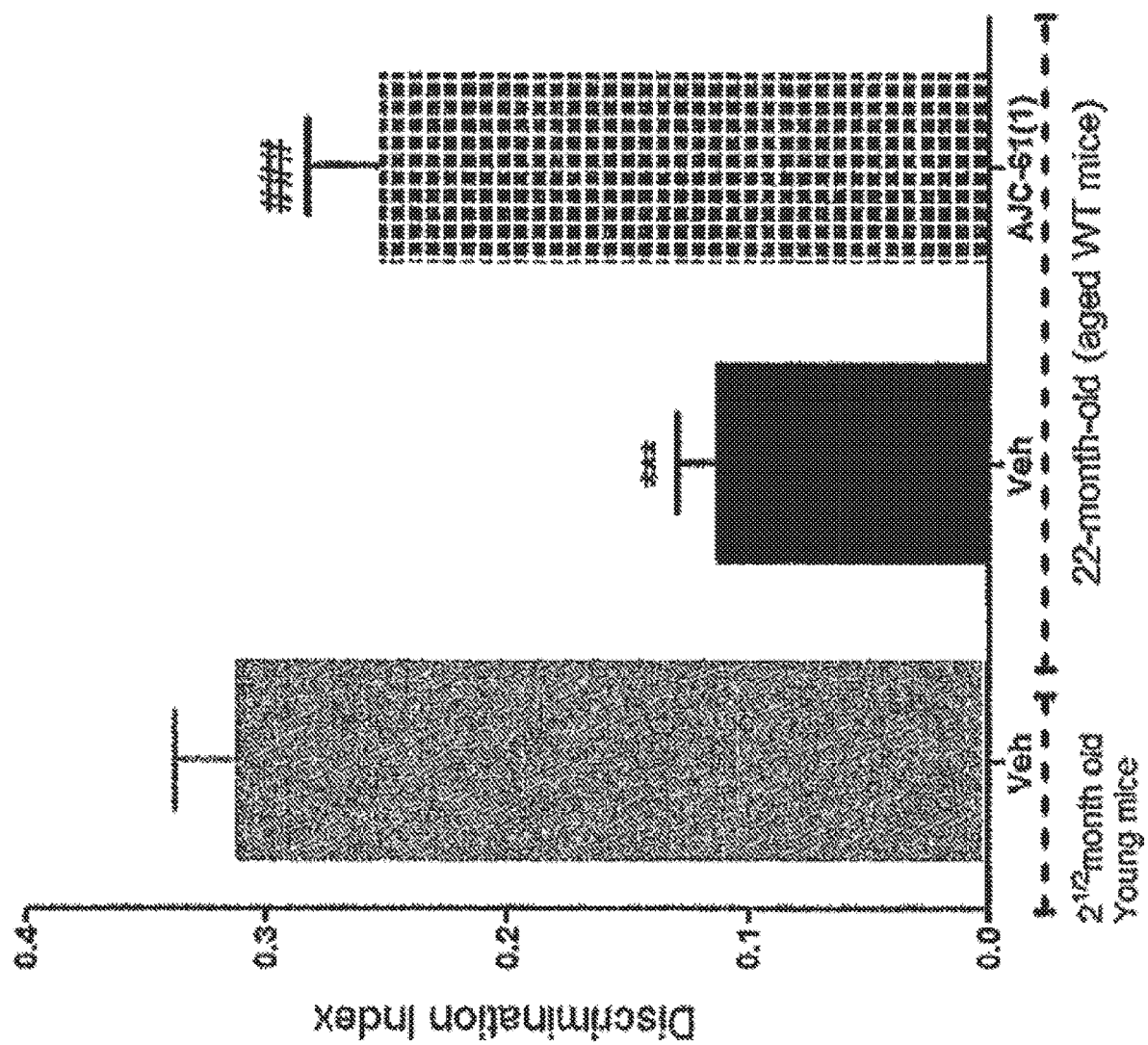

FIG. 8. Novel Object Recognition: Effect on discrimination index (DI) of Vehicle and AJC-61 (2 mg/kg) on 2.5 month old mice and 22-month old mice Data are shown as mean±S.E.M. of exploration time (s): n=14 pairs of mice per group. Significant difference were observed in the DI: *** p<0.001: Significant decrease in the DI for 22-month old mice versus 2.5 month old mice; ###p<0.001: Significant increase in the DI for 22-month old mice treated with AJC-61 versus Vehicle.

DETAILED DESCRIPTION

The disclosed subject matter further may be described utilizing terms as defined below.

Unless otherwise specified or indicated by context, the terms "a", "an", and "the" mean "one or more." For example, "a modulator of human serotonin receptor 2C (5-HT$_{2c}$) activity" should be interpreted to mean "one or more modulators of human serotonin receptor 2C (5-HT$_{2c}$) activity."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The terms "subject," "patient," and "individual" may be used interchangeably herein. A subject may be a human subject. A subject may refer to a human subject having or at risk for acquiring a disease, disorder, or condition, that is associated with human serotonin receptor 2C (5-HT$_{2c}$) activity. In specific embodiments, the disease, disorder, or condition is a psychiatric, mental, and/or neurological disease, disorder, or condition. Psychiatric, mental, and/or neurological disease, disorders, or conditions may include, but are not limited to, cognitive impairment, addiction, and obsessive compulsive disorder (OCD). The disclosed small molecules also may be administered to treat and/or prevent obesity, for example, via appetite suppression, where the treated and/or prevented disorder or condition is an eating disorder and/or obesity.

As used herein, the term "modulate" means decreasing or inhibiting activity and/or increasing or augmenting activity. For example, modulating human serotonin receptor 2C (5-HT$_{2c}$) activity may mean increasing or augmenting human serotonin receptor 2C (5-HT$_{2c}$) activity and/or decreasing or inhibiting human serotonin receptor 2C (5-HT$_{2c}$) activity. Preferably, the disclosed novel molecules increase or augment human serotonin receptor 2C (5-HT$_{2c}$) activity as positive allosteric ligands or agonists.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

New Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., —(CH$_2$)$_n$— where n is an integer such as an integer between 1 and 20). An exemplary alkylene group is —CH$_2$CH$_2$-.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C (O)N(R²)R³—, —C(O)NR²R³, or —C(O)NH₂, wherein R¹, R² and R³, for example, are each independently alkoxy, alkyl, alkenyl, alkynyl, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Beta-Carboline Compounds and Uses Thereof for Modulating 5-HT$_{2c}$ Receptor Activity The compounds disclosed herein may be referred to as beta-carboline compounds and in particular, substituted beta-carboline compounds. Optionally, the disclosed compounds may be saturated at one or more bonds to form dihydro-beta-carboline compounds or tetrahydro-beta-carboline compounds.

In some embodiments, the disclosed compound may be described as compounds or a salts or solvates thereof having a Formula I:

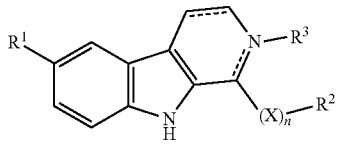

I where:
n is 0 or 1;
X is CH₂, NH, or O;
R¹ is selected from hydrogen, hydroxyl, alkyl (e.g. methyl), alkoxy (e.g., methoxy), halo (e.g., fluoro, chloro, bromo, iodo), haloalkyl (e.g., trifluoromethyl), amino, alkylamino, and cyano;
R² is hydrogen, alkyl, or a 3-7 membered carbocycle or heterocycle which is saturated or unsaturated at one or more bonds and which heterocycle includes one or more heteroatoms selected from N, O, and S, optionally which carbocycle or heterocycle is substituted to include one or more non-hydrogen substituents, which non-hydrogen substituents optionally are selected from alkyl (e.g. methyl), alkoxy (e.g., methoxy), halo (e.g., fluoro, chloro, bromo, iodo), haloalkyl (e.g., trifluoromethyl), hydroxyl, phenyl, amino, and carbonyl.

R³ is present or absent, and when R³ is present, R³ is selected from selected from hydrogen, alkyl (e.g., methyl), alkenyl (e.g. propenyl), and alkyl-alkoxy (e.g., propanyl-methoxy).

In some embodiments, the disclosed compounds may have a Formula Ia:

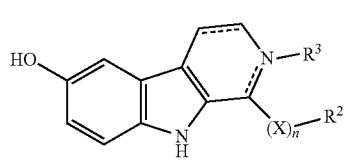

Ia

In some embodiments, the disclosed compound have a Formula Ib:

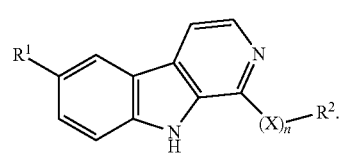

Ib

In the disclosed compounds, in some embodiments, R¹ may be selected from hydrogen, alkyl (e.g., methyl), alkyoxy (e.g., methoxy), and halo (e.g., chloro).

In the disclosed compounds, in some embodiments R¹ is selected from:

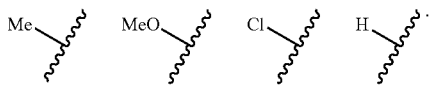

The compound of claim 1, wherein R² is selected from phenyl, cyclohexyl, pyridinyl (e.g., N-pyridinyl, pyridin-2-yl, pyridin-3-yl, or pyridin-4-yl), pyrimidinyl (e.g., pyrimidin-1-yl, pyrimidin-2-yl, pyrimidin-4-yl, or pyrimidin-5-yl), imidazolyl (e.g., imidazole-1-yl, imidazol-2-yl, or imidazole-4-yl), 1-methylimidazolyl (e.g., 1-methylimidazol-2-yl, 1-methylimidazol-3-yl, 1-methylimidazol-4-yl, or 1-methylimidazol-5-yl), piperidinyl (e.g., piperidin-2-yl, or piperidin-4-yl), 1-methyl-piperidinyl (1-methyl-piperidin-2-yl, 1-methyl-piperidin-3-yl, 1-methyl-piperidin-4-yl), piperazinyl (e.g., piperazin-1-yl, piperazin-2-yl, or piperazin-4-yl), 1-methyl-piperazinyl (e.g., 1-methyl-piperazin-2-yl, 1-methyl-piperazin-3-yl, or 1-methyl-piperazin-4-yl), tetrahydropyranyl (e.g., tetrahydropyran-2-yl, tetrahydropyran-3-yl, or, tetrahydropyran-4-yl), and morpholinyl (e.g., morpholin-2-yl, morpholin-3-yl, or morpholin-4-yl).

In the disclosed compounds, in some embodiments —(X)ₙ—R² is selected from:

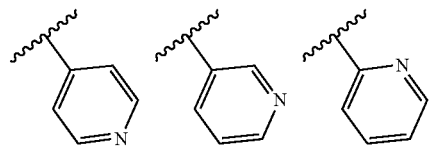

-continued

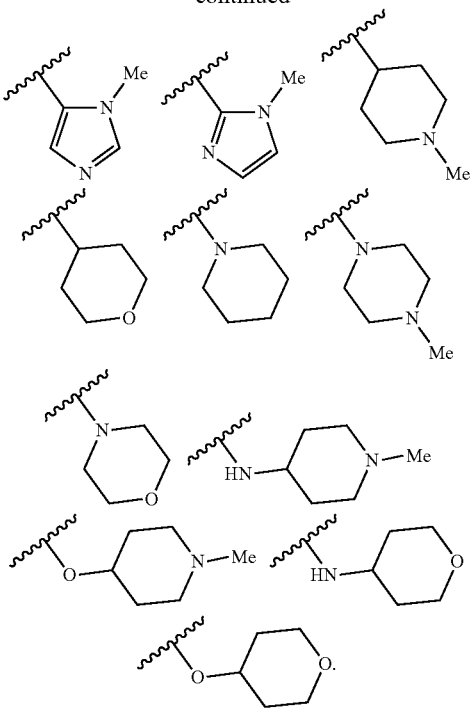

As noted, the compounds disclosed herein, including the substituted beta-carboline compounds discussed above may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, 99% or 100% pure stereoisomer, epimer, or enantiomer.) As used herein, formulae which do not specify the orientation at one or more chiral centers are meant to encompass all orientations and mixtures thereof.

Human Serotonin Receptor 2C (5-$HT_{2c}$) Activity Modulation

The compounds disclosed herein preferably modulate human serotonin receptor 2C (5-$HT_{2c}$) activity and may be administered to a subject in need thereof to modulate 5-$HT_{2c}$ receptor activity. Modulation may include activating or increasing human serotonin receptor 2C (5-$HT_{2c}$) activity. Modulation also may include inhibiting or decreasing human serotonin receptor 2C (5-$HT_{2c}$) activity.

5-$HT_{2c}$ receptor activity may be assessed utilizing methods known in the art and the methods disclosed herein, including the methods disclosed in the Examples provided herein. In some embodiments, the compounds decrease or increase 5-$HT_{2c}$ activity relative to a control (e.g., by at least about 10%, 20%, 30%, 40%, 50%, 60%, 70%, 80%, 90%, 100%, 200%, 300%, 400%, 500%, 600%, 700%, 800%, 900%, 1000% or more (or within a range bounded by any of these values)). In other embodiments, the compounds activate the 5-$HT_{2c}$ receptor greater than about 2-fold, 3-fold, 4-fold, 5-fold, 10-fold, 20-fold, 30-fold, 40-fold, 50-fold, 60-fold, 70-fold, 80-fold, 90-fold, or 100-fold, relative to a control. In other embodiments, the compounds activate the 5-$HT_{2c}$ receptor with a maximum activation ($E_{max}$) greater than about 100%, 200%, 300%, 400%, 500%, 600%, 700%, 800%, 900%, 1000%, 1100%, 1200%, 1300%, 1400%, or 1500% (or within a range bounded by any of these values). In other embodiments, an $EC_{50}$ value for the compound in regard to activation of the 5-$HT_{2c}$ receptor may be determined and preferably the compound has an $EC_{50}$ value of less than about 10 µM, 5 µM, or 1 µM, 0.5 µM, 0.1 µM, 0.05 µM, 0.01 µM, 0.005 µM, or 0.001 µM (or within a range bounded by any of these values). In other embodiments, $K_i$ value for the compound in regard to activation of the 5-$HT_{2c}$ receptor may be determined and preferably the compound has an $K_i$ value of less than about 10 µM, 5 µM, or 1 µM, 0.5 µM, 0.1 µM, 0.05 µM, 0.01 µM, 0.005 µM, or 0.001 µM (or within a range bounded by any of these values).

In some embodiments, the compounds disclosed herein do not bind to and/or activate or inhibit the 5-$HT_{2a}$ receptor or the 5-$HT_{2b}$ receptor or any other receptor other than the 5-$HT_{2c}$ receptor. If the compounds bind to and/or activate the 5-$HT_{2a}$ receptor or the 5-$HT_{2b}$ receptor or any other receptor, preferably the compounds have an $EC_{50}$ for the 5-$HT_{2a}$ receptor or the 5-$HT_{2b}$ receptor or any other receptor that is greater than about 0.01 µM, 0.05 µM, 0.1 µM, 0.5 µM, 1 µM, 10 µM, 20 µM, 50 µM, 100 µM, 200 µM, 500 µM, or 1000 µM If the compounds bind to and/or activate the 5-$HT_{2a}$ receptor or the 5-$HT_{2b}$ receptor or any other receptor, preferably the compounds have a for the 5-$HT_{2a}$ receptor or the 5-$HT_{2b}$ receptor or any other receptor that is greater than about 0.01 µM, 0.05 µM, 0.1 µM, 0.5 µM, 1 µM, 10 µM, 20 µM, 50 µM, 100 µM, 200 µM, 500 µM, or 1000 µM.

Pharmaceutical Compositions and Methods of Administration

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates the 5-$HT_{2c}$ receptor activity may be administered as a single compound or in combination with another compound that modulates the 5-$HT_{2c}$ receptor activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic, carbonic acid, succinic acid, citric acid, benzoic acid, acetic acid, and the like. Examples of suitable pharmaceutically acceptable salts may include the sulfate, pyrosulfate, bi sulfate, sulfite, bi sulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-. 1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating and/or preventing a disease, disorder, or condition associated with $5\text{-HT}_{2c}$ receptor activity. For example, the pharmaceutical compositions may be utilized to treat patients having or at risk for acquiring a psychiatric disease or disorder or condition. Suitable patients include, for example mammals, such as humans and non-human primates (e.g., chimps) or other mammals (e.g., dogs, cats, horses, rats, and mice). Suitable human patients may include, for example, those who have previously been determined to be at risk of having or developing a psychiatric disease, disorder, or condition associate with $5\text{-HT}_{2c}$ receptor activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to $-30°$ C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| | |
|---|---|
| Active Ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| | |
|---|---|
| Active Ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| Active Ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| | |
|---|---|
| Active Ingredient | 100 mg |
| Mannitol | 100 mg |
| 5N Sodium hydroxide | 200 ml |
| Purified water to total | 5 ml |

ILLUSTRATIVE EMBODIMENTS

The followings Embodiments are illustrative only and are not intended to limit the scope of the claimed subject matter.

Embodiment 1. A compound or a salt or solvate thereof having a Formula I:

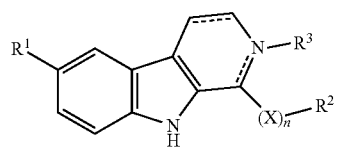

wherein:

n is 0-3;

X is $CH_2$, NH, or O;

$R^1$ is selected from hydrogen, hydroxyl, alkyl, alkoxy, halo, haloalkyl, amino, and cyano;

$R^2$ is hydrogen, or alkyl, or a 3-7 membered carbocycle or heterocycle which is saturated or unsaturated at one or more bonds and which heterocycle includes one or more heteroatoms selected from N, O, and S, optionally which carbocycle or heterocycle is substituted to include one or more non-hydrogen substituents, which non-hydrogen substituents optionally are selected from hydroxyl, alkyl, halo, haloalkyl, phenyl, amino, and carbonyl.

$R^3$ is present or absent, and when $R^3$ is present, $R^3$ is selected from selected from hydrogen, alkyl, alkenyl, and alkyl-alkoxy.

Embodiment 2. The compound of embodiment 1 having Formula Ia:

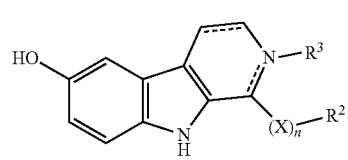

Embodiment 3. The compound of embodiment 1 having a Formula Ib:

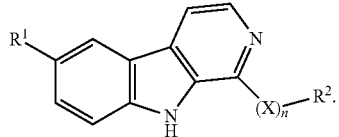

Embodiment 4. The compound of embodiment 1 having a Formula Ic:

Embodiment 5. The compound of embodiment 1 having a Formula Id:

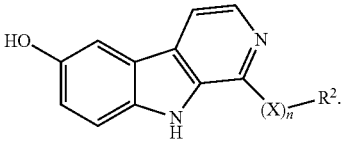

Embodiment 6. The compound of embodiment 1 having a Formula Ie:

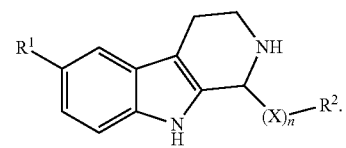

Embodiment 7. The compound of embodiment 1, wherein $R^1$ is selected from hydrogen, alkyl, hydroxyl, alkyoxy, and halo.

Embodiment 8. The compound of embodiment 4, wherein $R^1$ is selected from:

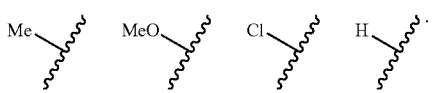

Embodiment 9. The compound of embodiment 1, wherein $R^2$ is selected from phenyl, cyclohexyl, pyridinyl, pyrimidinyl, imidazolyl, 1-methylimidazolyl; piperidinyl, 1-methyl-piperidinyl, piperazinyl, 1-methyl-piperazinyl, tetrahydropyranyl, and morpholinyl.

Embodiment 10. The compound of embodiment 1, wherein $—(X)_n—R^2$ is selected from:

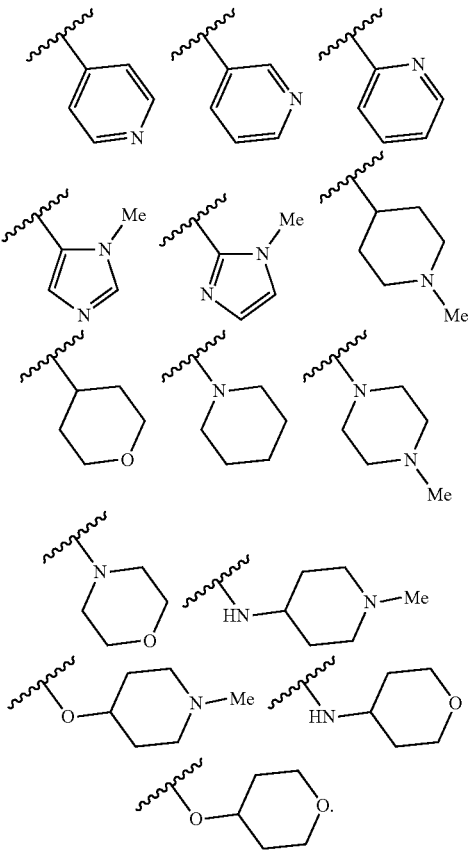

Embodiment 11. The compound of embodiment 5, wherein $—(X)_n—R^2$ is selected from:

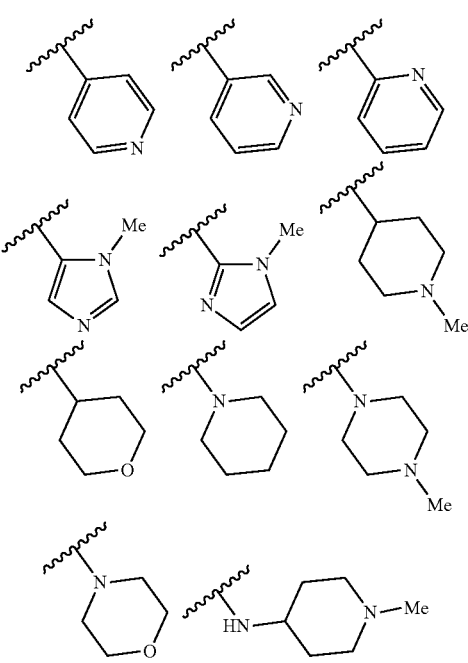

-continued

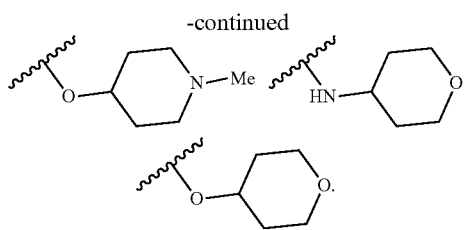

Embodiment 12. The compound of any of the foregoing embodiments with the proviso that at least one of $R^1$, $R^2$, and $R^3$ is not hydrogen.

Embodiment 13. The compound of embodiment 1 having a formula:

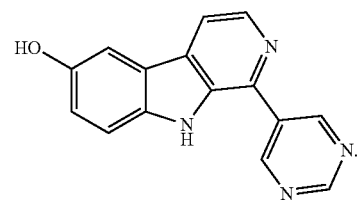 [SMILES: Oc1ccc2[nH]c3c(-c4cncnc4)nccc3c2c1]

Embodiment 14. The compound of embodiment 1 having a formula selected from:

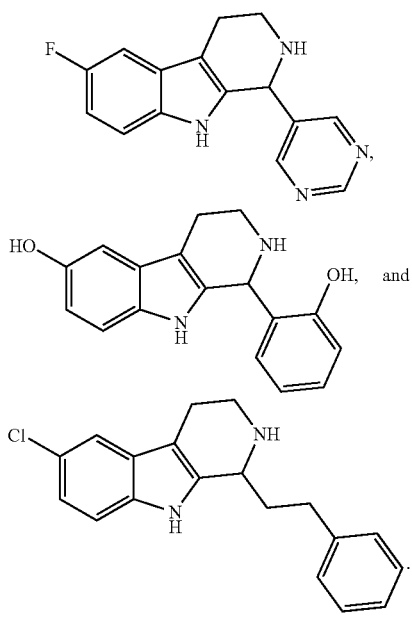

Embodiment 15. A compound having a formula of any of the compounds of embodiments 1-14 or a compound having a formula of any compound disclosed in this application for use in treating and/or preventing a disease, disorder, or condition that is associated with 5-$HT_{2c}$ receptor activity in a subject in need thereof.

Embodiment 16. A pharmaceutical composition comprising any of the compounds of the foregoing embodiments and a pharmaceutical carrier.

Embodiment 17. A method for treating and/or preventing a disease, disorder, or condition that is associated with 5-$HT_{2c}$ receptor activity in a subject in need thereof, the method comprising administering to the subject the compound of any of embodiments 1-15 or the pharmaceutical composition of embodiment 16.

Embodiment 18. The method of embodiment 17, wherein the disease or disorder is a psychiatric, mental, or neurological disease, disorder, or condition.

Embodiment 19. The method of embodiment 17, wherein the disease, disorder, or condition is cognitive impairment, addiction, and/or obsessive compulsive disorder (OCD).

Embodiment 20. The method of embodiment 17, wherein the disease, disorder, or condition is obesity and the method results in suppressing the appetite of the subject.

EXAMPLES

The followings Examples are illustrative only and are not intended to limit the scope of the claimed subject matter.

Beta-Carbolines as Positive Allosteric Modulators of the Human Serotonin Receptor 2c (5-$HT_{2c}$)

Technical Field

The technical field of the disclosed subject matter relates to small molecule drug development. The disclosed small molecules provide a drug platform that has potential to treat cognitive impairment, addiction, obsessive compulsive disorder, and obesity via appetite suppression.

Abstract

We disclose novel small molecules having a substituted beta-carboline core. The disclosed small molecules have potential for treating cognitive impairment (CI), for which there is currently no direct treatment. The disclosed small molecules also have potential for treating addition. Although there are several drug options for treating addiction depending on the addiction, many are inadequate. For example, the current opioid epidemic exists despite the existence of treatment options that include methadone, buprenorphinem and naltrexone. The disclosed small molecules also have potential for treating obsessive compulsive disorder (OCD). OCD is most often treated with antidepressant medications, but often patients do not respond to these medications. Electroconvulsive therapy can be tried in these cases, but this therapy is largely regarded as ineffective.

Applications

Applications of the disclosed small molecules include, but are not limited to treatment of a range of neurological disorders and diseases that are associated with 5-$HT_{2c}$ activity. Disorders and diseases that may be treated with the disclosed small molecules may include cognitive impairment (CI), addiction, and obsessive compulsive disorder (OCD). The disclosed small molecules also may suppress appetite and therefore may be administered to treat obesity and eating disorders.

Advantages

There currently is only one FDA-approved drug that acts selectively on 5-$HT_{2c}$, Lorcaserin, which currently is approved only for weight loss. However, Lorcaserin is associated with two dangerous side effects: cancer and cardiac valvulopathy. While Lorcaserin demonstrates selectivity for 5-$HT_{2c}$, Lorcaserin nonetheless exhibit activity for 5-$HT_{2a}$ and 5-$HT_{2b}$.

| Receptor | $EC_{50}$ [nM] | $K_i$ [nM] |
| --- | --- | --- |
| 5-$HT_{2C}$ | 39 | 13 |
| 5-$HT_{2B}$ | 2380 | 147 |
| 5-$HT_{2A}$ | 553 | 92 |

While Lorcaserin's selectivity for 5-HT$_{2c}$=39 nM) over 5-HT$_{2a}$ (K$_i$=92 nM) and 5-HT$_{2b}$ (K$_i$=147 nM) is good, selectivity can be improved upon because positive allosteric modulators have been known to bind less conserved sites.

Brief Summary of the Technology

Small molecules have been designed having a substituted beta-carboline core and based on known yohimbine natural products alstonine and serpentine. The disclosed small molecules exhibit in vivo activity consistent with agonism or positive allosteric modulation of the serotonin receptor 5-HT$_{2c}$.

Compound Synthesis

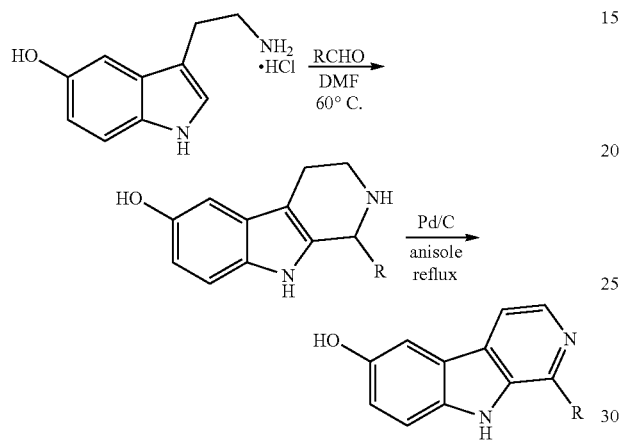

General Procedure A: Pictet-Spengler reaction of serotonin•HCl and aldehydes to give tetrahydro-β-carbolines. To a solution of serotonin hydrochloride (1 equiv) in N,N-dimethylformamide (4.5 mL/mmol serotonin hydrochloride) was added the appropriate aldehyde (1.1 equiv). The resulting solution was stirred at 60° C. overnight (16-20 hours). After this time the reaction was allowed to cool to room temperature, neutralized with saturated sodium bicarbonate (equal volume to N,N-dimethylformamide), and was extracted with ethyl acetate (3×equal volumes of the total mixture). The combined organic layers were washed with additional water (1 equal volume), washed with saturated sodium chloride (1 equal volume), dried over magnesium sulfate, filtered, and concentrated to dryness. The resulting residue was purified via column chromatography.

General Procedure B: Palladium on carbon aromatization of tetrahydro-β-carbolines to give β-carbolines. To a flask containing dry tetrahydro-β-carboline (1 equiv) and palladium on carbon (10 wt %, 0.1 equiv) was added anisole (15 mL/mmol of tetrahydro-β-carboline). The resulting mixture was heated at reflux overnight (16-20 hours). If the reaction had not proceeded sufficiently, minimal amounts of methanol were added to aid with solubility, and the reaction was resubmitted to the previous conditions. After this time the reaction was allowed to cool to room temperature, filtered through Celite® (rinsing with methanol), and concentrated to dryness. The resulting residue was purified via column chromatography.

General Procedure C: Alkylation of β-carbolines to give N-alkyl β-carbolines. To a solution of β-carboline (1 equiv) in N,N-dimethylformamide (7 mL/mmol of β-carboline) was added the appropriate alkyl halide (1.1 equiv). The resulting mixture was heated at 85° C. overnight (16-20 hours). After this time the reaction was allowed to cool to room temperature. If starting material was not consumed, additional alkyl halide would be added and resubmitted to the previous conditions. After this time, the reaction was concentrated to dryness. The resulting residue was purified via column chromatography.

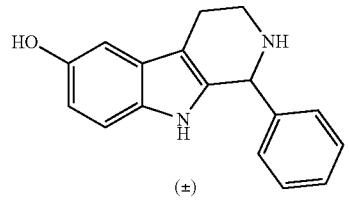 [SMILES: Oc1ccc2[nH]c3c(c2c1)CCNC3c1ccccc1]

1-phenyl-1H,2H,3H,4H,9H-pyrido[3,4-b]indol-6-ol was synthesized according to general procedure A and was purified on 10 g silica gel, with a gradient of dichloromethane to 6% methanol/94% dichloromethane to give the title product (0.120 g, 32%) as an off-white solid; $^1$H NMR (500 MHz, DMSO-d$_6$) δ 10.04 (s, 1H), 8.51 (s, 1H), 7.37-7.21 (m, 6H), 7.16 (dd, J=18.3, 7.3 Hz, 1H), 6.99 (d, J=8.5 Hz, 1H), 6.72 (s, 1H), 6.50 (dd, J=8.5, 2.2 Hz, 1H), 5.02 (s, 1H), 3.05-3.01 (m, 1H), 2.93-2.88 (m, 1H), 2.67-2.62 (m, 1H), 2.59-2.54 (m, 1H). $^{13}$C NMR (126 MHz, DMSO) δ 150.15, 143.31, 135.85, 130.36, 128.38, 128.03, 127.51, 127.07, 111.25, 110.36, 107.43, 101.82, 56.65, 41.25, 21.05. MS (ESI) calculated for C$_{17}$H$_{17}$N$_2$O [M+H]$^+$: 265.1, Found: 265.2.

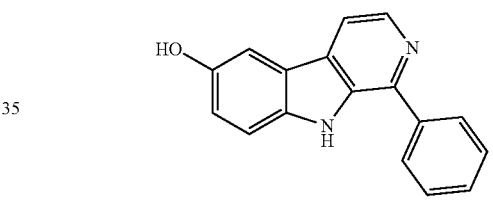

1-phenyl-9H-pyrido[3,4-b]indol-6-ol was synthesized according to general procedure B and was purified on 10 g silica gel, with a gradient of [10 g silica, dichloromethane to 4% methanol/96% dichloromethane to give the title product (0.359 g, 53%) as a tan solid; $^1$H NMR (500 MHz, DMSO-d$_6$) δ 11.18 (s, 1H), 9.15 (s, 1H), 8.37 (d, J=5.1 Hz, 1H), 8.00 (dd, J=10.9, 6.4 Hz, 3H), 7.60 (t, J=7.5 Hz, 2H), 7.55-7.42 (m, 3H), 7.07 (dd, J=8.7, 2.2 Hz, 1H). $^{13}$C NMR (126 MHz, DMSO) δ 151.03, 141.96, 138.53, 137.56, 137.34, 135.17, 133.55, 128.83, 128.66, 128.38, 128.26, 121.43, 118.26, 112.96, 105.41. MS (ESI) calculated for C$_{17}$H$_{13}$N$_2$O [M+H]$^+$: 261.1, Found: 262.1.

6-hydroxy-1-phenyl-2-(prop-2-en-1-yl)-9H-pyrido[3,4-b]indol-2-ium bromide was synthesized according to general procedure C and was purified on 25 g silica gel, with a gradient of dichloromethane to 7% methanol/93% dichloromethane to give the title product (0.143 g, 64%) as a dark yellow solid; $^1$H NMR (500 MHz, DMSO-$d_6$) δ 11.98 (s, 1H), 9.69 (s, 1H), 8.80 (d, J=6.6 Hz, 1H), 8.69 (d, J=6.6 Hz, 1H), 7.76 (m, 6H), 7.53 (d, J=8.9 Hz, 1H), 7.33 (dd, J=8.9, 2.4 Hz, 1H), 6.20-5.73 (m, 1H), 5.26 (d, J=10.5 Hz, 1H), 5.08 (d, J=5.2 Hz, 2H), 4.95 (d, J=17.2 Hz, 1H). $^{13}$C NMR (126 MHz, DMSO) δ 152.55, 140.09, 139.09, 135.27, 132.53, 132.43, 131.74, 131.35, 129.66, 129.40, 128.23, 123.16, 120.33, 119.23, 117.22, 113.92, 105.91, 58.69. MS (ESI) calculated for $C_{20}H_{17}N_2O$ [M]$^+$: 301.1, Found: 301.3.

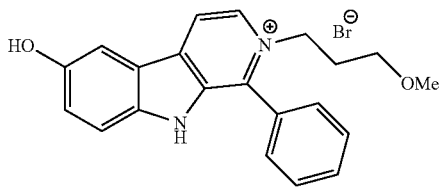 [SMILES: COCCC[n+]1ccc2c([nH]c3ccc(O)cc32)c1-c1ccccc1 ; [Br-]]

6-hydroxy-2-(3-methoxypropyl)-1-phenyl-9H-pyrido[3,4-b]indol-2-ium bromide was synthesized according to general procedure C and was purified on 10 g silica gel, with a gradient of dichloromethane to 20% methanol/80% dichloromethane to give the title product (0.045 g, 28%) as a dark brown solid; $^1$H NMR (500 MHz, DMSO-$d_6$) δ 11.90 (s, 1H), 9.67 (s, 1H), 8.78-8.73 (m, 2H), 7.79-7.74 (q, J=17.8, 11.1 Hz, 6H), 7.52 (d, J=8.9 Hz, 1H), 7.32 (dd, J=8.9, 2.3 Hz, 1H), 4.49 (t, J=7.4 Hz, 2H), 3.22 (t, J=5.8 Hz, 2H), 3.06 (s, 3H), 1.98 (p, J=6.1 Hz, 2H). $^{13}$C NMR (126 MHz, DMSO) δ 152.51, 139.98, 138.91, 135.27, 132.50, 131.47, 131.25, 129.69, 129.51, 128.38, 123.00, 120.30, 117.09, 113.88, 105.91, 68.16, 57.68, 54.57, 30.32. MS (ESI) calculated for $C_{21}H_{21}N_2O_2$ [M]$^+$: 333.2, Found: 333.3.

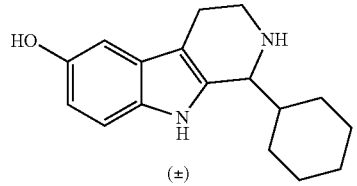 [SMILES: Oc1ccc2[nH]c3c(c2c1)CCNC3C1CCCCC1]

1-cyclohexyl-1H,2H,3H,4H,9H-pyrido[3,4-b]indol-6-ol was synthesized according to general procedure A and was purified on 10 g silica gel, with a gradient of dichloromethane to 20% methanol/80% dichloromethane to give the title product (0.083 g, 22%) as a tan solid; $^1$H NMR (500 MHz, DMSO-$d_6$) δ 10.66 (s, 1H), 8.70 (s, 1H), 7.48-6.95 (m, 1H), 6.73 (s, 1H), 6.62-6.60 (m, 1H), 4.43 (s, 1H), 3.48-3.46 (m, 1H), 3.25-3.15 (m, 1H), 2.98-2.73 (m, 2H), 2.20-2.10 (m, 1H), 1.82-1.65 (m, 4H), 1.38-1.10 (m, 7H). $^{13}$C NMR (126 MHz, DMSO) δ 150.65, 130.66, 130.06, 126.69, 111.64, 111.57, 105.93, 101.93, 57.36, 41.84, 29.23, 26.66, 26.08, 25.71, 18.58. MS (ESI) calculated for $C_{17}H_{23}N_2O$ [M+H]$^+$: 271.2, Found: 271.0.

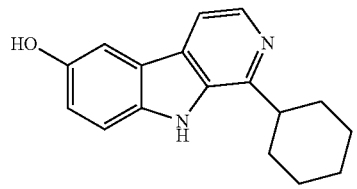 [SMILES: Oc1ccc2[nH]c3c(C4CCCCC4)nccc3c2c1]

1-cyclohexyl-9H-pyrido[3,4-b]indol-6-ol was synthesized according to general procedure B and was purified on 50 g silica gel, with a gradient of dichloromethane to acetone to give the title product (0.093 g, 31%) as a beige solid; $^1$H NMR (500 MHz, DMSO-$d_6$) δ 11.17 (s, 1H), 9.06 (s, 1H), 8.15 (d, J=5.2 Hz, 1H), 7.77 (d, J=5.2 Hz, 1H), 7.44 (d, J=2.2 Hz, 1H), 7.40 (d, J=8.7 Hz, 1H), 7.04 (dd, J=8.7, 2.4 Hz, 1H), 3.28-3.20 (m, 1H), 1.91-1.82 (m, 2H), 1.81-1.66 (m, 3H), 1.56-1.41 (m, 2H), 1.39-1.25 (m, 1H). $^{13}$C NMR (126 MHz, DMSO) δ 150.68, 149.74, 136.68, 134.39, 133.78, 126.82, 121.75, 117.77, 112.38, 112.37, 105.43, 40.80, 31.31, 26.24, 25.84. MS (ESI) calculated for $C_{17}H_{19}N_2O$ [M+H]$^+$: 267.2, Found: 267.4.

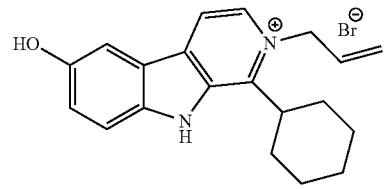 [SMILES: C=CC[n+]1ccc2c([nH]c3ccc(O)cc32)c1C1CCCCC1 ; [Br-]]

1-cyclohexyl-6-hydroxy-2-(prop-2-en-1-yl)-9H-pyrido[3,4-b]indol-2-ium bromide was synthesized according to general procedure C and was purified on 10 g silica gel, with a gradient of dichloromethane to acetone to give the title product (0.066 g, 46%) as a dark yellow solid; $^1$H NMR (500 MHz, DMSO-$d_6$) δ 12.00 (s, 1H), 9.65 (s, 1H), 8.63 (d, J=6.5 Hz, 1H), 8.56 (d, J=6.2 Hz, 1H), 7.73 (d, J=8.9 Hz, 1H), 7.68 (d, J=2.2 Hz, 1H), 7.36 (dd, J=8.9, 2.4 Hz, 1H), 6.25-6.17 (m, 1H), 5.51 (s, 2H), 5.36 (d, J=10.6 Hz, 1H), 5.02 (d, J=17.3 Hz, 1H), 3.50-3.39 (m, 1H), 2.35-2.16 (m, 2H), 2.01-1.62 (m, 6H), 1.53-1.40 (m, 2H). $^{13}$C NMR (126 MHz, DMSO) δ 152.51, 146.40, 138.08, 133.81, 133.21, 133.15, 132.32, 123.06, 119.76, 118.00, 116.14, 113.94, 105.56, 59.72, 48.58, 27.96, 25.71, 23.96. MS (ESI) calculated for $C_{20}H_{23}N_2O$ [M]$^+$: 307.2, Found: 307.3.

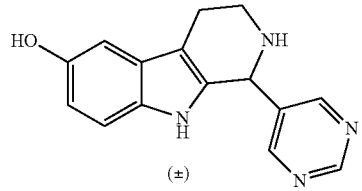 [SMILES: Oc1ccc2[nH]c3c(c2c1)CCNC3c1cncnc1]

1-(pyrimidin-5-yl)-1H,2H,3H,4H,9H-pyrido[3,4-b]indol-6-ol was synthesized according to general procedure A and was purified on 10 g silica gel, with a gradient of dichloromethane to 10% methanol/90% dichloromethane to give the title product (0.137 g, 37%) as an off-white solid; $^1$H NMR (500 MHz, DMSO-$d_6$) δ 10.23 (s, 1H), 9.12 (s, 1H), 8.67 (s, 2H), 8.58 (s, 1H), 7.02 (d, J=8.5 Hz, 1H), 6.75 (d, J=2.0 Hz, 1H), 6.55 (dd, J=8.5, 2.2 Hz, 1H), 5.14 (s, 1H), 3.14-2.92 (m, 3H), 2.74-2.64 (m, 1H), 2.64-2.55 (m, 2H). $^{13}$C NMR (126 MHz, DMSO) δ 157.33, 156.69, 150.36, 136.39, 134.06, 130.45, 127.44, 111.35, 110.84, 108.06, 102.01, 52.39, 41.38, 22.03. MS (ESI) calculated for $C_{15}H_{15}N_4O$ [M+H]$^+$: 267.1, Found: 267.2.

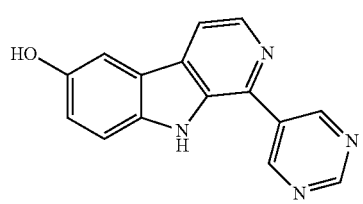 [SMILES: Oc1ccc2[nH]c3c(-c4cncnc4)nccc3c2c1]

1-(pyrimidin-5-yl)-9H-pyrido[3,4-b]indol-6-61 (AJC-61) was synthesized according to general procedure B and was purified on 25 g silica gel, with a gradient of dichloromethane to 50% acetone/50% dichloromethane to give the title product (0.024 g, 5%) as a yellow solid; $^1$H NMR (500 MHz, DMSO-$d_6$) δ 11.54 (s, 1H), 9.40 (s, 2H), 9.32 (s, 1H), 9.23 (s, 1H), 8.51-8.40 (m, 1H), 8.19-8.06 (m, 1H), 7.57 (s, 1H), 7.47 (d, J=8.7 Hz, 1H), 7.11 (d, J=8.6 Hz, 1H). $^{13}$C NMR (126 MHz, DMSO) δ 157.83, 156.08, 151.29, 138.05, 136.13, 135.29, 134.04, 132.02, 129.36, 121.28, 118.76, 115.10, 112.96, 105.64. MS (ESI) calculated for $C_{15}H_{11}N_4O$ [M+H]$^+$: 263.1, Found: 263.1.

TABLE 1

Activity of Selected Compounds.

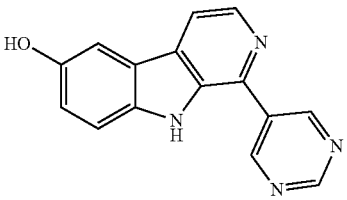 [SMILES: Oc1ccc2[nH]c3c(-c4cncnc4)nccc3c2c1]

AJC-61

| | |
|---|---|
| 2C agonist | inactive |
| antagonist | >10 μM |
| 2A agonist | inactive |
| antagonist | no data |

TABLE 1-continued

Activity of Selected Compounds.

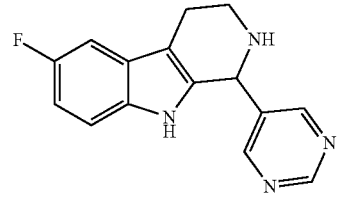 [SMILES: Fc1ccc2[nH]c3c(c2c1)CCNC3c1cncnc1]

MJO-01-31

| | |
|---|---|
| 2C agonist | 10.1 nM |
| Emax | 101% |
| 2A agonist | 54.6 nM |
| Emax | 95% |

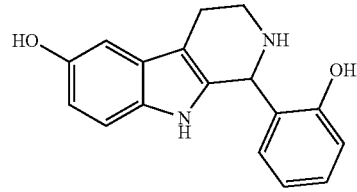 [SMILES: Oc1ccc2[nH]c3c(c2c1)CCNC3c1ccccc1O]

MJO-01-34

| | |
|---|---|
| 2C agonist | 85.9 nM |
| Emax | 103% |
| 2A agonist | 106 nM |
| Emax | 27% |

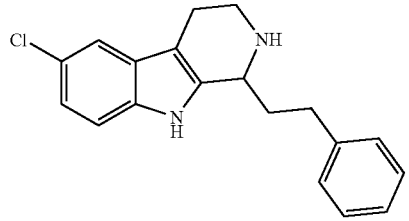 [SMILES: Clc1ccc2[nH]c3c(c2c1)CCNC3CCc1ccccc1]

MJO-01-46

| | |
|---|---|
| 2C agonist | 5.37 nM |
| Emax | 98% |
| 2A agonist | 11.3 nM |
| Emax | 96% |

Scheme 1. Targets in Progress

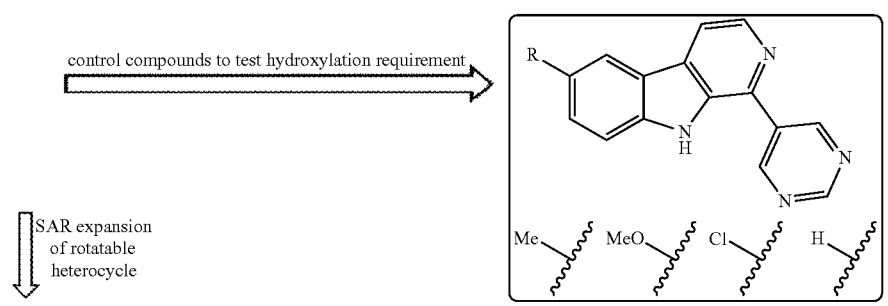

-continued

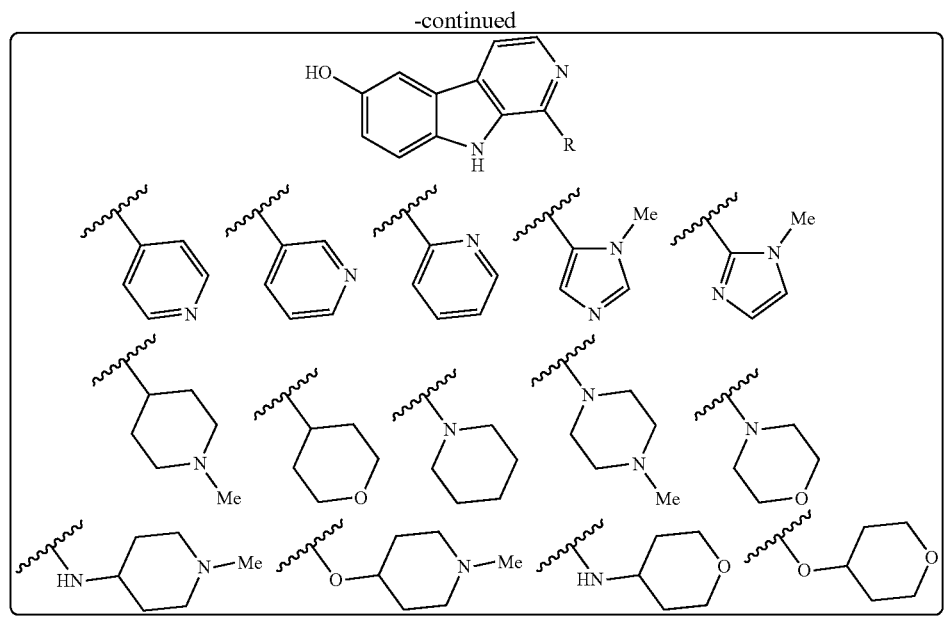

Biological Activity of AJC-61

Mouse models were utilized to demonstrate the potential of compound AJC-61 in treating and or affecting psychotic spectrum disorder-schizophrenia including cognitive impairment of schizophrenia, negative symptoms of schizophrenia including deficit in social interaction, bipolar disorder, major depression including psychotic major depression, locomotor activity suppression-specific for positive (psychotic) symptoms of schizophrenia, psychoses of Alzheimer's disease and Parkinson's disease, obsessive compulsive disorder, Tourette's syndrome, and age-associated cognitive impairment.

Figure 1:
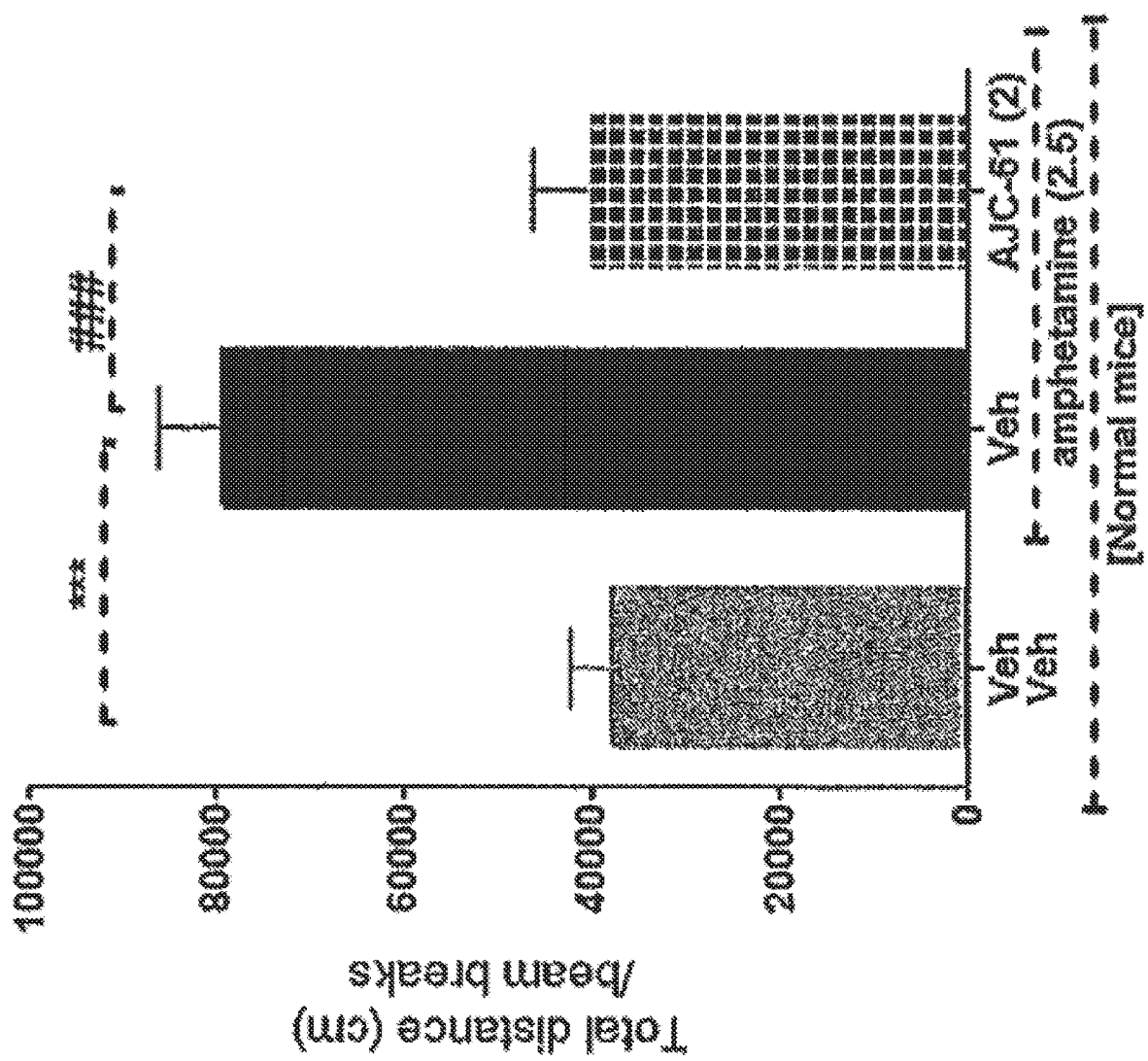
FIG. 1. Locomotor Activity: AJC-61 blocked amphetamine-induced increase in locomotor activity in mice. The effect of AJC-61 (2 mg/kg) on amphetamine-induced (2.5 mg/kg) increase in locomotor activity in mice. Data are presented as group means±S.E.M. for eight successive 15 minute intervals. *** p<0.001: significant increase in LMA versus Vehicle+Vehicle; ###p<0.001: significant decrease in LMA versus Vehicle+AJC-61 (2 mg/kg)+amphetamine (2.5 mg/kg).
Figure 2:
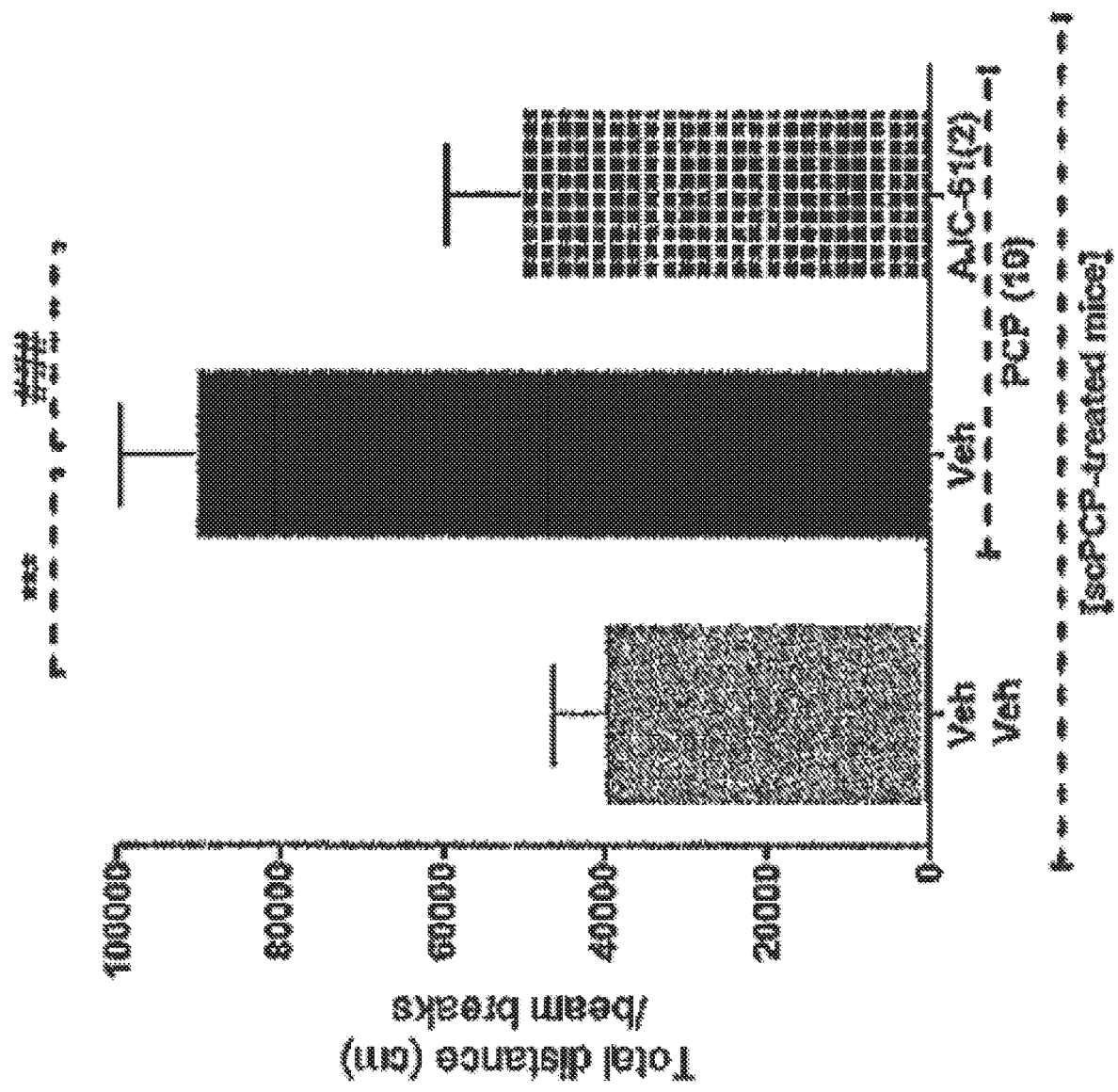
FIG. 2. Locomotor Activity: AJC-61 blocked PCP-induced increase in locomotor activity in mice. The effect of AJC-61 (2 mg/kg) on PCP-induced (10 mg/kg) increase in locomotor activity in mice. Data are presented as group means±S.E.M. for eight successive 15 minute intervals. *** p<0.001: significant increase in LMA versus Vehicle+Vehicle; ###p<0.001: significant decrease in LMA versus Vehicle+AJC-61 (2 mg/kg)+PCP (10 mg/kg). sc—subchronic.

The ability of a test drug to block the increase in Locomotor Activity (LMA) produced by amphetamine or the glutamate receptor agonist, phencyclidine (PCP), has a high predictive value for the antipsychotic efficacy of the test drug for treating schizophrenia. Administration of amphetamine or PCP to man has been shown to produce psychotic state in a significant percentage of previously normal humans. Treatment of mice with PCP for one week has been shown to produce a robust model of schizophrenia. As such, we tested the effect of AJC-61 on reducing LMA in mice that had been treated with amphetamine or PCP to increase LMA activity. As shown in FIG. 1, AJC-61 blocked the amphetamine-induced increase in LMA in mice, and as shown in FIG. 2, AJC-61 blocked the PCP-induced increase in LAM in mice.

Figure 3:
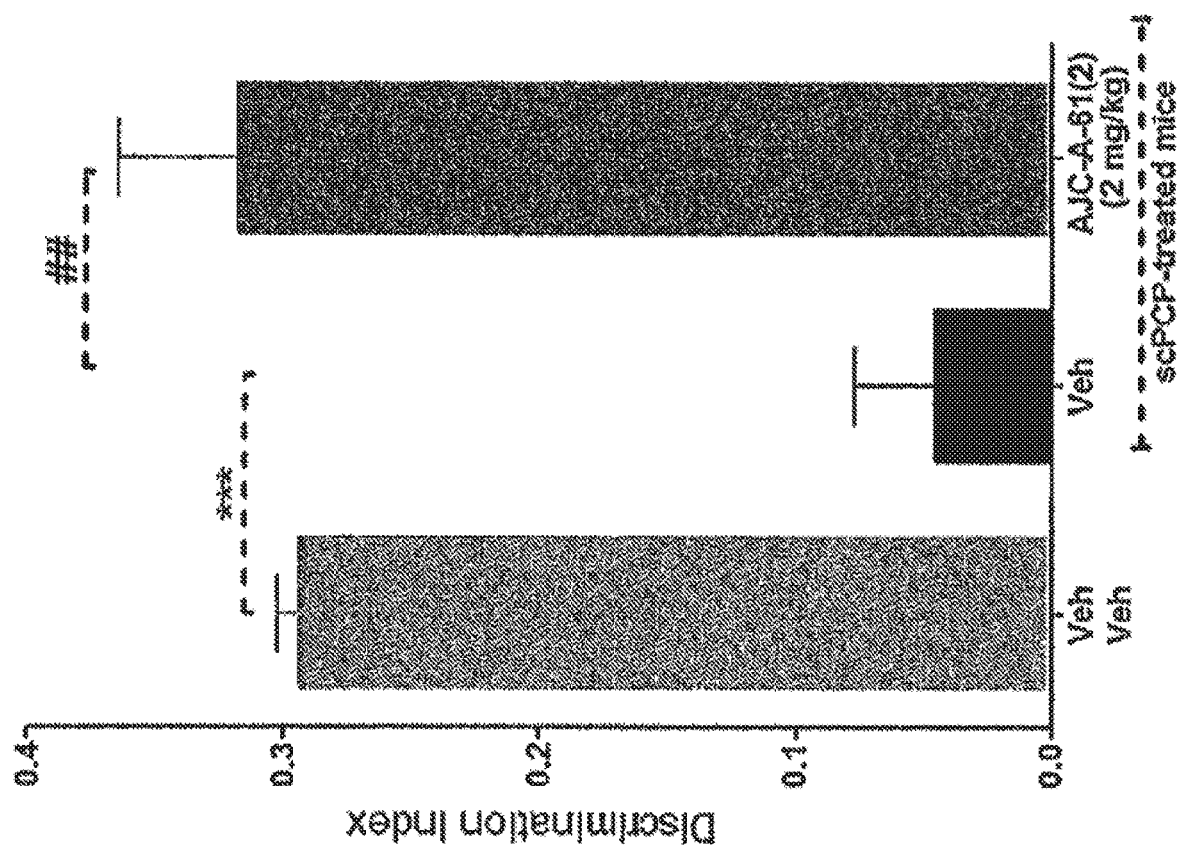
FIG. 3. Novel Object Recognition: Discrimination index (DI) for male C57BL/6J mice treated with Vehicle, PCP (10 mg/kg), and PCP+AJC-61 (2 mg/kg). Data are shown as mean±S.E.M. of exploration time (s) n=10 mice per group.

The Novel Object Recognition test in rodents is considered a valid model of spatial memory in man. The time spent viewing an object seen previously versus the time spent viewing a novel object (i.e., the Discrimination Index (DI)) provides an indirect measure of assessing retention of the memory of the object that had previously been shown to the rodent. Normal mice remember for ~24 hours. The time to loss of the memory in aged mice can be as low as zero to less than 8 hours. As such, we tested the effect of AJC-61 on reducing the DI in mice that had been treated with PCP to reduce the DI. As shown in FIG. 3, we observed a significant increase in DI in the PCP+AJC-61-treated mice versus the PCP-treated mice.

A healthy mouse will vigorously explore a newly introduce mouse and retain the memory for that mouse for up to 24 hours. The loss of interest in exploring a novel mouse is considered a sign of negative symptoms.

PCP-treatment produces a deficit in social interaction which models negative symptoms in schizophrenia. These include lack of motivation, loss of interest in activities, diminished capacity for pleasure and spontaneous activity. We tested the effect of AJC-61 on Social Interaction in mice that had been treated with PCP, including a Social Behaviors that include sniffing, following, and avoiding and Object Exploration via interaction with an inanimate object. As illustrated in FIG. 4, regarding sniffing we observed a significant reduction in sniffing for the PCP group versus the Vehicle group, and a significant increase in sniffing for the PCP+AJC-61 versus group versus the PCP group. Regarding following, we observed no significant change, although there was non-significant reduction in following in the PCP group versus the Vehicle group. Regarding avoiding, we observed a significant increase for the PCP versus group versus the Vehicle group, and a significant decrease in avoiding for the PCP+AJC-61 group versus the PCP group. Regarding object exploration, we observed no significant change, although there was a non-significant increase in object exploration in the PCP group versus the Vehicle group.

The Porsolt Forced Swim Test (FST) is a gold standard test for antidepressant action. In the FST, normal mice become immobile after being required to swim in a tank and begin to float instead of struggling to get out of the water. Antidepressant drugs have been shown to increase the amount of time that a mouse will continue to swim prior to floating. As such, we tested whether AJC-61 could increase the swim time in a FST. As illustrated in FIG. 5, treatment with PCP significantly increased the immobility time whereas treatment with PCP+AJC-61 significantly decreased the immobility time.

Marble Burying (MB) and extent of shredding a standard type of rodent bedding (i.e., Nestlet Shredding) are both proven methods for assessing drug efficacy to treat obsessive-compulsive disorder and Tourette's syndrome. As such, we tested the effect on AJC-61 on Marble Burying and Nestlet Shredding. As illustrated in FIG. 6, we observed a significant increase in the number of marbles buried for the PCP group versus the Vehicle group, and we observed a significant decrease in the number of marbles buried for the PCP+AJC-16 group versus the PCP group. As illustrated in FIG. 7, we observed a significant increase in the percent nestlet shredded for the PCP group versus the Vehicle group, and we observed a significant decrease in the percent nestlet shredded for the PCP+AJC-16 group versus the PCP group.

Aged mice show a decline in memory function beginning around 13-15 month of age. Drugs which enhance memory can be assessed using the Novel Object Recognition test and determination of the Discrimination Index (DI) as discussed above. As such, we tested whether AJC-61 could improve the DI for aged mice (i.e., 22-month old mice) versus young mice (i.e., 2.5 month old mice). As illustrated in FIG. 8, we observed a significant decrease in the DI for 22-month old mice versus the DI for 2.5 month old mice, and we observed a significant increase in the DI for 22-month old mice when the mice were treated with AJC-61.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A compound or a salt or solvate thereof having a Formula I:

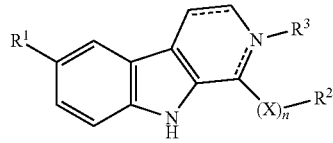

wherein:
n is 0-3;
X is $CH_2$, NH, or O;
$R^1$ is selected from hydrogen, hydroxyl, alkyl, alkoxy, halo, haloalkyl, amino, and cyano;
$R^2$ is pyrimidin-5-yl; and
$R^3$ is present or absent, and when $R^3$ is present, $R^3$ is selected from selected from hydrogen, alkyl, alkenyl, and alkyl-alkoxy.

2. The compound of claim 1 having Formula Ia:

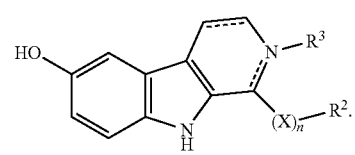

3. The compound of claim 1 having a Formula Ib:

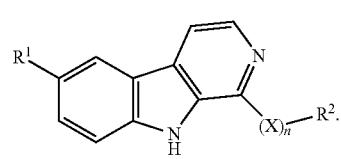

4. The compound of claim 1 having a Formula Ic:

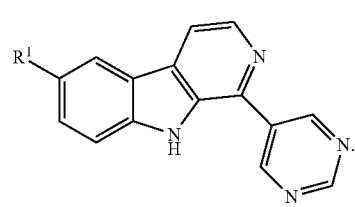

5. The compound of claim 1 having a Formula Id:

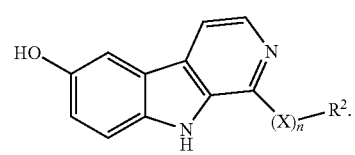

6. The compound of claim 1 having a Formula Ie:

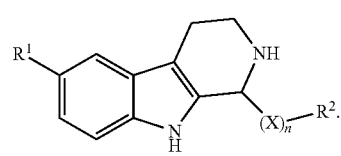

7. The compound of claim 1, wherein $R^1$ is selected from hydrogen, alkyl, hydroxyl, alkoxy, and halo.

8. The compound of claim 1, wherein $R^1$ is selected from:

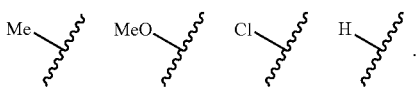

9. The compound of claim 1 having a formula:

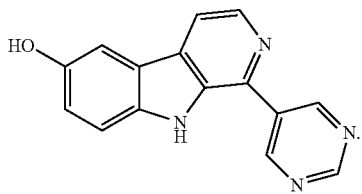 [SMILES: Oc1ccc2[nH]c3c(-c4cncnc4)nccc3c2c1]

10. The compound of claim 1 having a formula selected from:

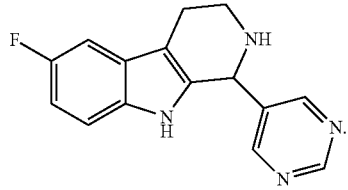 [SMILES: Fc1ccc2[nH]c3c(c2c1)CCNC3c1cncnc1]

11. The compound of claim 1 for use in treating and/or preventing a disease, disorder, or condition that is associated with 5-$HT_{2c}$ receptor activity in a subject in need thereof.

12. A pharmaceutical composition comprising the compound of claim 1 and a pharmaceutical carrier.

13. A method for treating and/or preventing a disease, disorder, or condition that is associated with 5-$HT_{2c}$ receptor activity in a subject in need thereof, wherein the disease or disorder is a psychiatric, mental, or neurological disease, disorder, or condition; wherein the disease, disorder, or condition is cognitive impairment, addiction, and/or obsessive compulsive disorder; or wherein the disease, disorder, or condition is obesity and the method results in suppressing the appetite of the subject, the method comprising administering to the subject the compound of claim 1.

14. The method of claim 13, wherein the disease or disorder is a psychiatric, mental, or neurological disease, disorder, or condition.

15. The method of claim 13, wherein the disease, disorder, or condition is cognitive impairment, addiction, and/or obsessive compulsive disorder.

16. The method of claim 13, wherein the disease, disorder, or condition is obesity and the method results in suppressing the appetite of the subject.

* * * * *